(12) United States Patent
Beck

(10) Patent No.: US 8,518,397 B2
(45) Date of Patent: Aug. 27, 2013

(54) NOTCH INDUCED NATURAL KILLER CELL GENERATION AND THERAPEUTIC USES

(75) Inventor: Rose C. Beck, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 12/855,203

(22) Filed: Aug. 12, 2010

(65) Prior Publication Data

US 2011/0044962 A1 Feb. 24, 2011

Related U.S. Application Data

(60) Provisional application No. 61/233,968, filed on Aug. 14, 2009.

(51) Int. Cl.
*A01N 63/00* (2006.01)
*C12N 5/00* (2006.01)

(52) U.S. Cl.
USPC ................ 424/93.71; 435/384; 435/405

(58) Field of Classification Search
USPC ................ 424/93.71; 435/384, 405
See application file for complete search history.

(56) References Cited

U.S. PATENT DOCUMENTS

2003/0153082 A1* 8/2003 Bhatia .................... 435/455
2005/0261477 A1* 11/2005 Champion et al. ........... 530/350

FOREIGN PATENT DOCUMENTS

WO WO 03/011317 A1 * 2/2003

OTHER PUBLICATIONS

Haraguchi et al. (Notch Activation Induces the Generation of Functional NK Cells from Human Cord Blood CD34-Positive Cells Devoid of IL-15. Journal of Immunology. Published May 15, 2009. 182: 6168-6178).*
Invitrogen Immunoprecipitation with Dynabeads Protein A.*
Meunch et al. (Differential effect of interleukin-3, interleukin-7, interleukin-15 and granulocyte-macrophage colony stimulating factor in the generation of natural killer and B cells from primitive human fetal liver progenitors. Experimental Hematology 2000. 28: 961-973).*
Bachanova et al., Activated Notch Supports Development of Cytokine Producing NK Cells which are Hyporesponsive and Fail to Acquire NK Cell Effector Functions, *Biol. Blood Marrow Transplant* 15:183-194 (2009).
Cooley et al., "A Subpopulation of Human Peripheral Blood NK Cells that Lacks Inhibitory Receptors for Self-MHC is Developmentally Immature", *Blood* 110:578-586 (2007).
Miller et al., "Successful Adoptive Transfer and In Vivo Expansion of Human Haploidentical NK Cells in Patients with Cancer", *Blood* 105:3051-3057 (2005).

* cited by examiner

*Primary Examiner* — Karen Cochrane Carlson
*Assistant Examiner* — Natalie Moss
(74) *Attorney, Agent, or Firm* — Tarolli, Sundheim, Covell & Tummino LLP

(57) ABSTRACT

A method of preparing differentiated NK cells by ex vivo expansion includes the steps of: (1) isolating a plurality of $CD34^+$ hematopoietic cells; (2) culturing the cells in a medium, wherein the medium includes an effective amount of a notch ligand and one or more cytokines selected from the group consisting of IL-7, IL-15, SCF, Flt-3, IL-3 and IL-6; and (3) maintaining the cells in culture for a duration of time sufficient to produce NK cells.

10 Claims, 14 Drawing Sheets

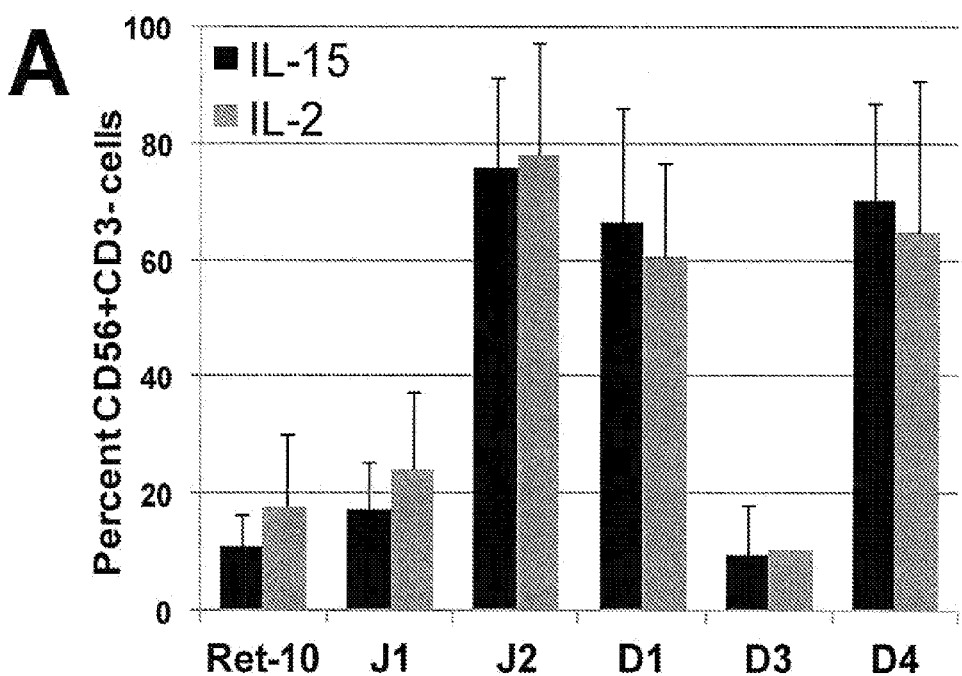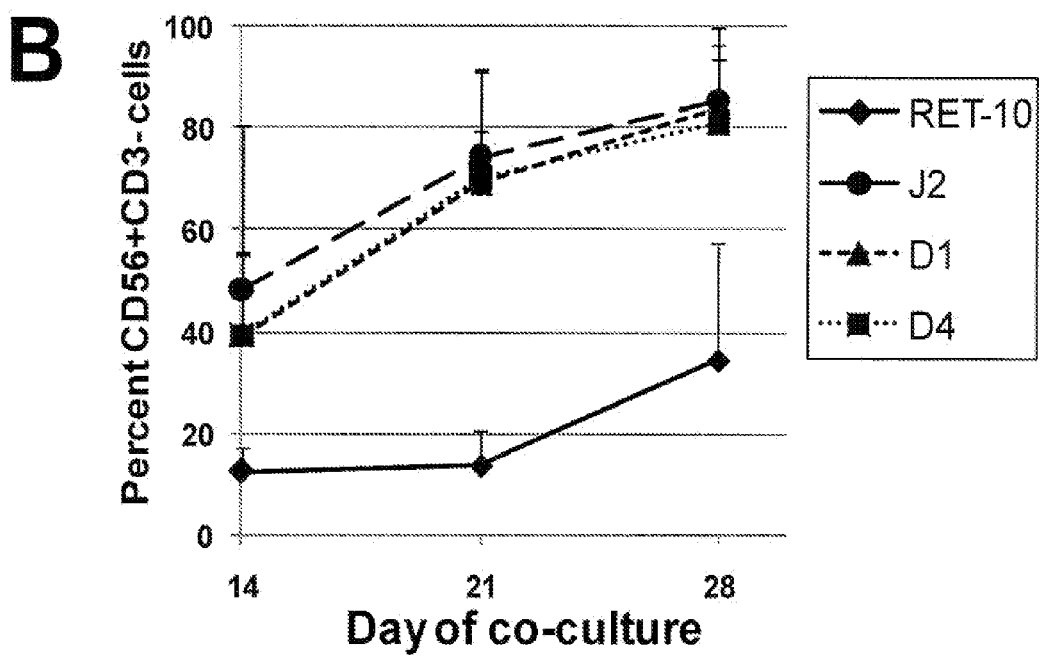
Fig. 1A-B

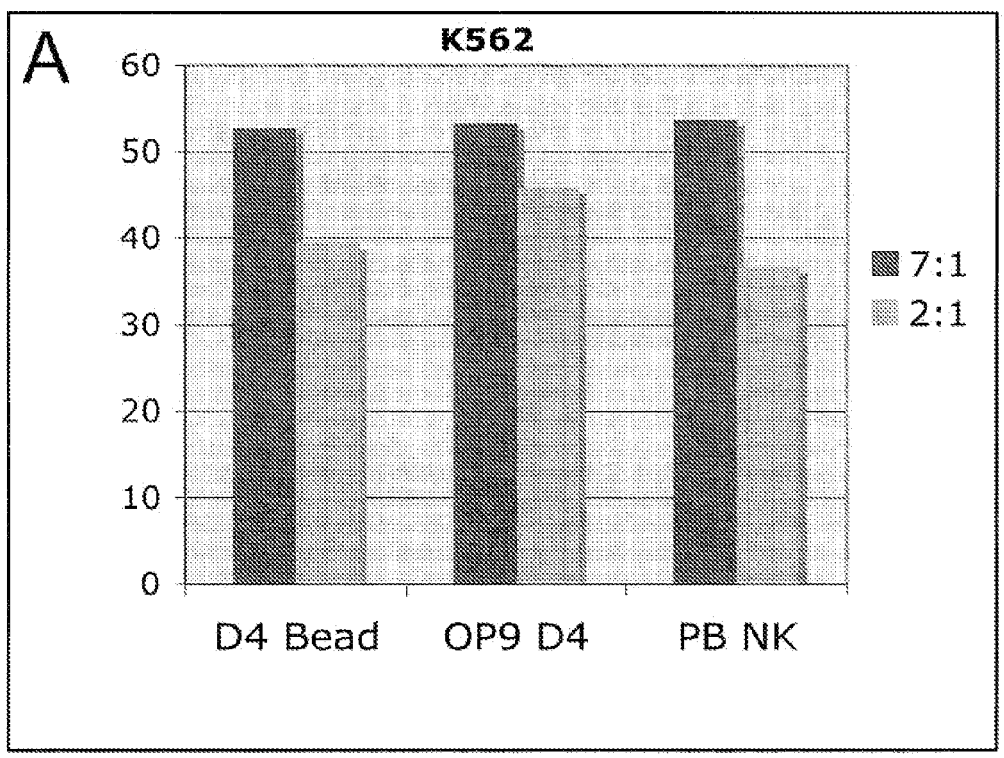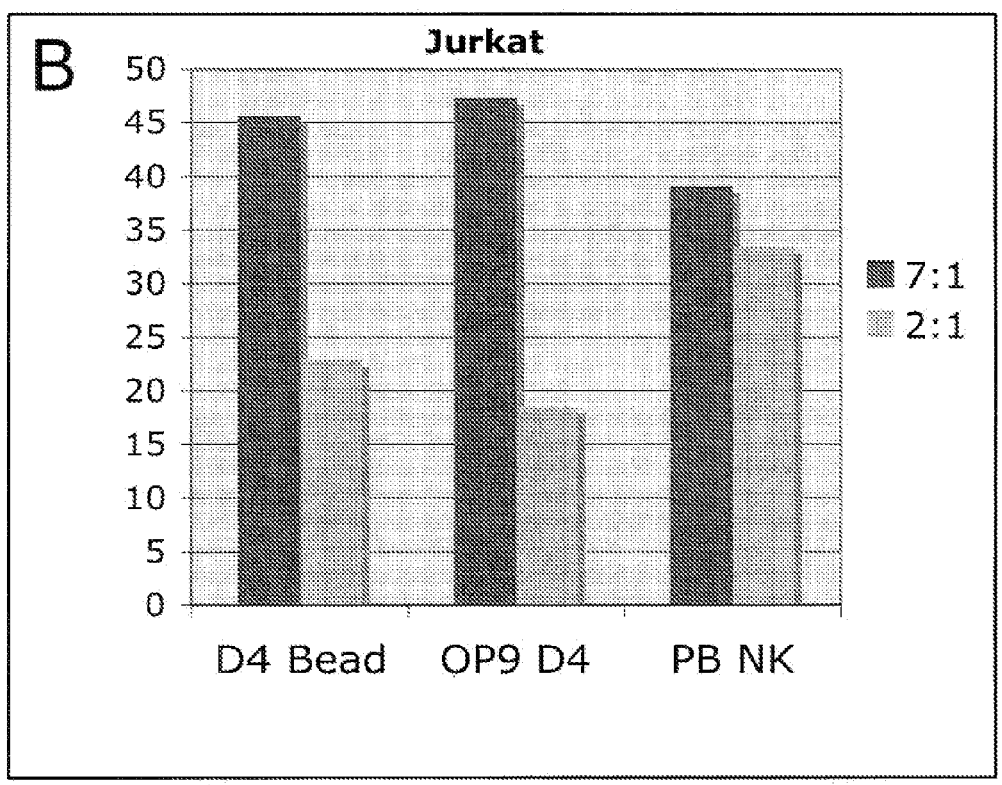
Figs. 9A-B

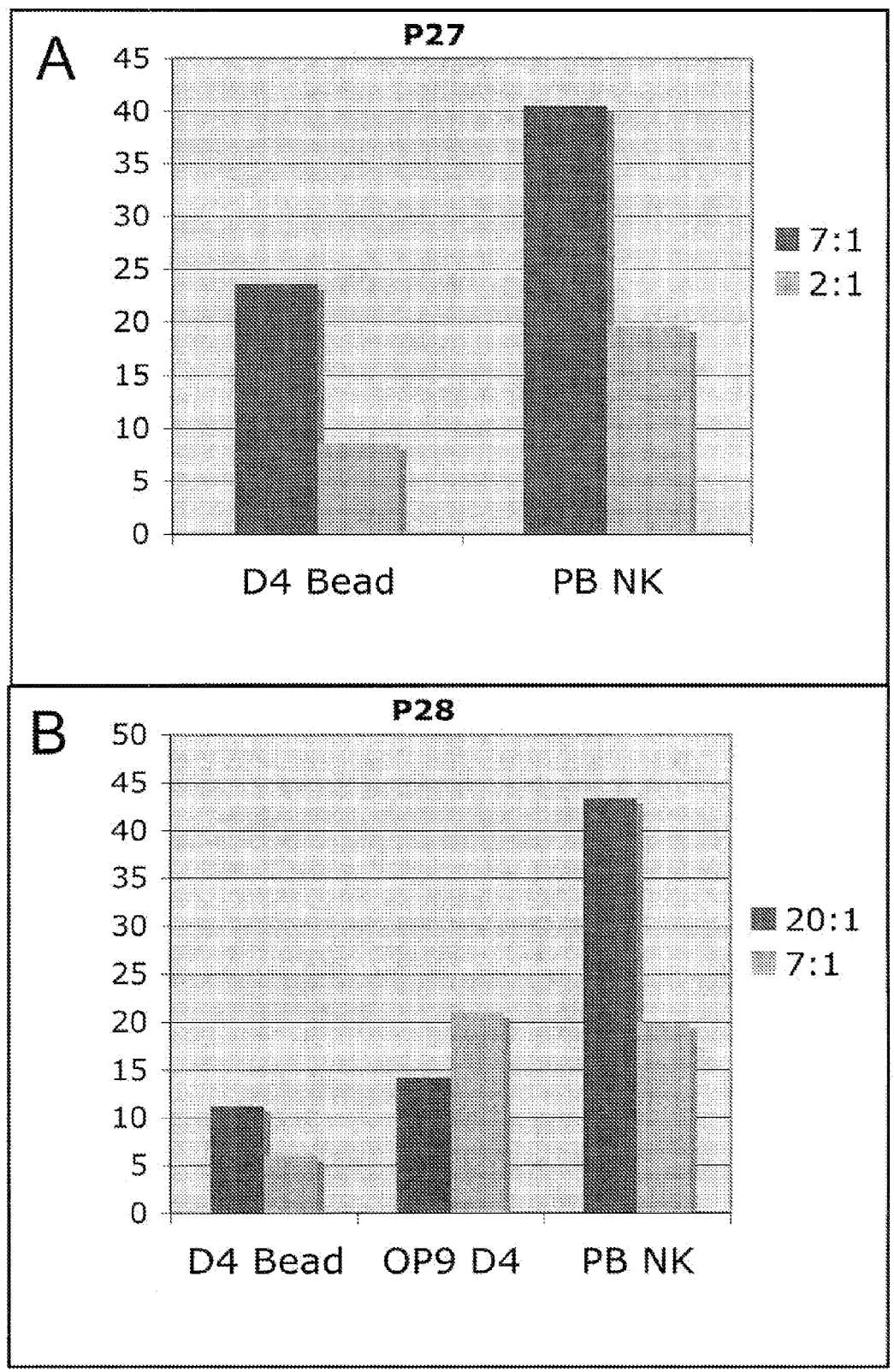
Figs. 11A-B

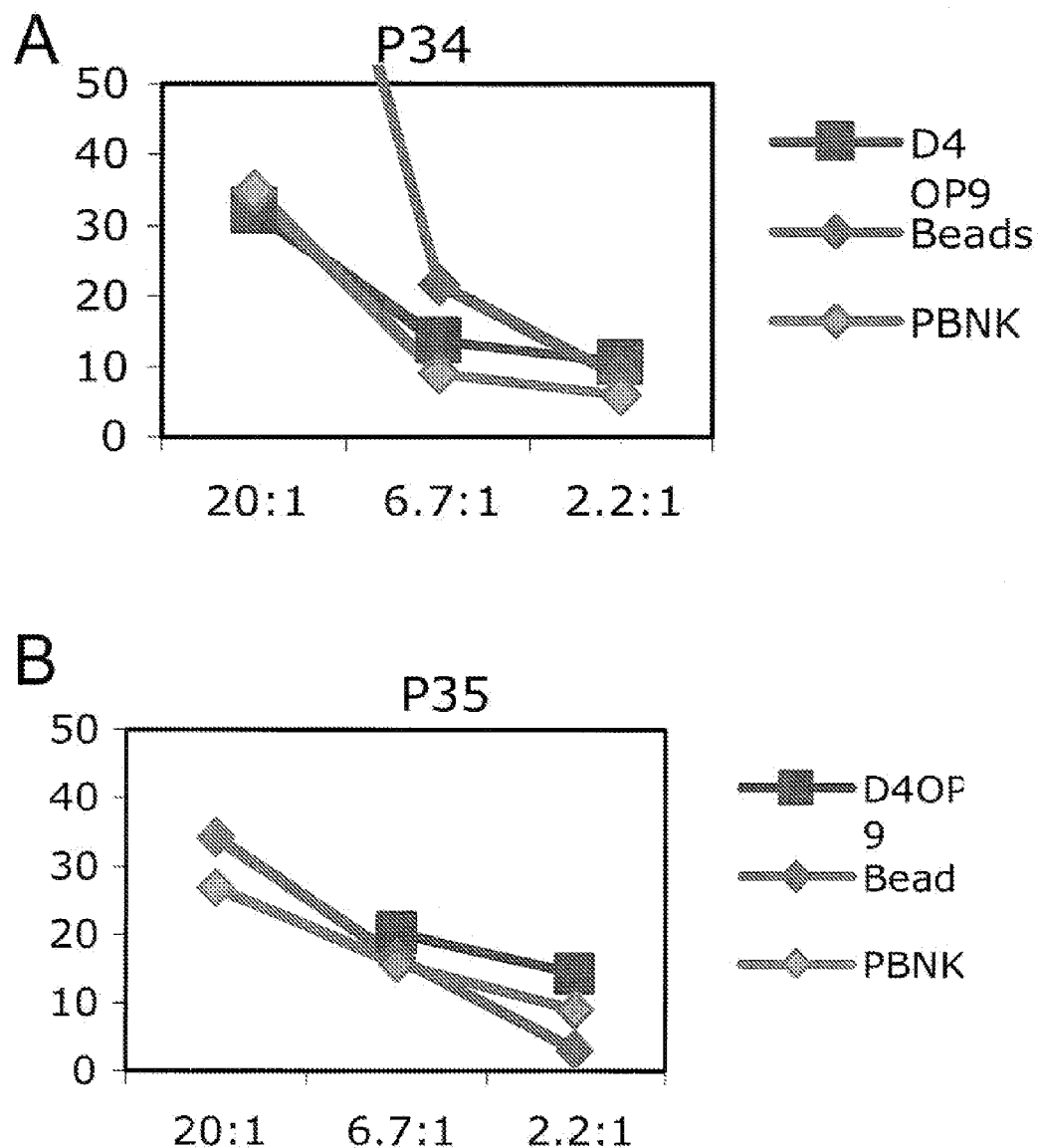
Figs. 12A-B

NOTCH INDUCED NATURAL KILLER CELL GENERATION AND THERAPEUTIC USES

RELATED APPLICATION

This application claims priority from U.S. Provisional Application No. 61/233,968, filed Aug. 14, 2009, the subject matter which is incorporated herein by reference.

BACKGROUND

Natural killer (NK) cells are lymphocytes, which arise from a common lymphoid progenitor cell during hematopoiesis. Unlike T and B lymphocytes, however, NK cells do not express rearranged antigen receptors and are therefore considered part of the innate immune system. NK cells have the unique ability to kill tumor or virally-infected cells without prior immunization. Another major function of NK cells is to secrete cytokines, such as IFN-γ and TNF-α, which augment inflammatory immune responses and also influence adaptive immunity.

Human NK cells are defined as CD56+CD3− lymphocytes, which morphologically are indistinguishable from CD8+ granular T cells. The circulating pool of NK cells in humans consists of two populations: $CD56^{dim}CD16^{bright}$ and $CD56^{bright}CD16^{dim}$. The former population is predominant (>95% of circulating NK cells), has more cytotoxic than cytokine-producing activity, and may represent a mature NK cell population which evolves from $CD56^{bright}CD16^{dim}$ cells (Cooper et al. Trends Immunol 2001; 22:633-640). Accordingly, $CD56^{bright}$ NK cells express CD117, higher levels of CD94 (which heterodimerizes with NKG2A (Natural Killer Group 2, member A) or NKG2C to form HLA-E recognition receptors), and CCR7, which may allow for NK cell trafficking to lymph nodes (Campbell et al. J. Immunol 2001; 166).

In contrast, $CD56^{dim}$ NK cells express higher levels of killer immunoglobulinlike receptors (KIRs) and the natural cytotoxicity receptors (NCRs), which include NKp30, NKp44, and NKp46, important for tumor cell recognition and lysis. $CD56^{dim}$ NK cells down-regulate expression of CCR7 and express CXCR1, which binds IL-8 and is postulated to aid in the $CD56^{dim}$ NK cell response to inflammation (Campbell et al. 2001). Members of the KIR family are critical for transmission of inhibitory signals to NK cells upon binding of self-MHC class I molecules, thus mediating self-tolerance of $CD56^{dim}$ NK cells. Expression of CD16, also known as the low-affinity IgG Fc receptor, also allows $CD56^{dim}$ NK cells to mediate antibody-dependent cell-mediated cytotoxicity in the presence of antibody specific to target cells. Both types of NK cells express NKG2D, a homodimeric activating receptor, which binds stress-inducible ligands on tumor cells.

It has been traditionally postulated that human NK cells develop in the bone marrow, but recent data suggest that NK cell precursors from the bone marrow may migrate to secondary lymphoid organs, where maturation of NK precursors into $CD56^{bright}$ NK cells can occur. The NK cell precursors identified in lymph nodes have been divided into subsets based on expression of CD34, CD94, and CD117 (Freud et al. Immunol Rev 2006; 214:56-72). In line with this hypothesis, $CD56^{bright}$ NK cells are found preferentially in lymph nodes and can express CD16, KIRs, and NCRs, as well as acquire cytotoxic activity, upon activation (Fehniger T A et al. Blood 2003; 101:3052-3057; Ferlazzo G, et al. J Immunol 2004; 172:1455-1462.

In vitro, both mouse and human NK cells can differentiate from bone marrow- or cord blood-derived hematopoietic progenitor cells (HPCs) in the presence of cytokines alone; these NK cells appear phenotypically immature and resemble $CD56^{bright}$ cells (Colucci et al. Nat Rev Immunol 2003; 3:413-425). Culture of HPCs in the presence of both cytokines and stromal cells allows for further maturation of NK cells, including acquisition of KIRs or the murine equivalent, the Ly49 receptor family (Cooley et al. Blood 2007; 110:578-586; Williams et al. J Immunol 1999; 163:2648-2656).

SUMMARY

The present invention relates to a method of preparing differentiated NK cells by ex vivo expansion. The method includes the step of isolating a plurality of CD34+ hematopoietic cells. In some embodiments, the CD34+ hematopoietic cells are derived from umbilical cord blood. The method also includes culturing the cells in a medium, wherein the medium includes an effective amount of a notch ligand and one or more cytokines selected from the group consisting of IL-7, IL-15, SCF, Flt-3 and IL-3. In some particular embodiments, the medium can further include IL-6. In some embodiments, the notch ligand is delta4 notch ligand.

In other embodiments the CD34+ are cultured in a stromal-cell free medium that includes a notch ligand immobilized on a substrate. In some aspects of the invention, the notch ligand can be immobilized on a solid substrate suspended in the medium, which facilitates interaction of the CD34+ cells and the notch ligand. In some embodiments, the solid substrate includes a plurality of protein A beads. In some embodiments the protein A beads are coated with notch ligand and used at a concentration of at least 0.01 µg/ml to 100 µg/ml.

The method further includes maintaining the cells in culture for a duration of time sufficient to produce NK cells. In some embodiments, the NK cells lack MHC class I inhibitory signals. In some particular embodiments, the NK cells do not express an inhibitory receptor surface protein selected from KIR and NKG2A. In some particular embodiments, the NK cells have at least the following characteristics: $CD56^{bright}$, CD16−, CD 117+, KIR−, $CD94^{low}$, CD11b−. In some embodiments, the duration of time is between about 2 and about 6 weeks. In other embodiments, the duration is about 4 weeks.

The present invention also relates to a substantially homogenous cell population of NK cells. In some embodiments, the population of NK cells lack MHC class I inhibitory signals. In some particular embodiments, the population of NK cells do not express an inhibitory receptor surface protein selected from KIR and NKG2A. In some particular embodiments, the NK cells have at least the following characteristics: $CD56^{bright}$, CD16−, CD117+, KIR−, $CD94^{low}$, CD11b−.

The present invention also relates to a method of treating cancer in a subject. The method includes administering to the subject a therapeutically effective amount of a substantially homogenous population of NK cells, wherein the NK cells are alloreactive and have at least the following characteristics: $CD56^{bright}$, CD16−, CD117+, KIR−, $CD94^{low}$, CD11b−. In some embodiments, the NK cells lack MHC class I inhibitory signals. In other embodiments, the substantially homogenous population of NK cells comprising greater than about 60% homogenous cells. In some embodiments, the NK cells are allogeneic. In other embodiments, the NK cells are autologous NK cells. In some embodiments, the NK cells are administered systemically. In other embodiments, the NK cells can be administered directly to a tumor site in the subject. In some embodiments, the cancer treated is selected from the group consisting of a solid tumor, carcinoma, and a hematological malignancy.

The present invention further relates to a method of treating cancer in a subject. The method includes administering to the subject a therapeutically effective amount of hematopoietic stem cells and a substantially homogenous cell population of NK cells. The NK cells have at least the following characteristics: $CD56^{bright}$, CD16−, $CD117^+$, KIR−, $CD94^{low}$, CD11b−. In some embodiments, the NK cells are alloreactive and have specific cytotoxic activity towards a host's antigen presenting cells, thereby inhibiting GVHD in the subject following hematopoietic stem cell transplantation. In some embodiments, the NK cells lack MHC class I inhibitory signals. In other embodiments, the substantially homogenous population of NK cells comprising greater than about 60% homogenous cells. In some embodiments, the hematopoietic cell population is allogeneic to the subject. In other embodiments, the hematopoietic cell population is autologous to the subject. In some embodiments, the NK cells are allogeneic to the subject. In other embodiments, the NK cells are autologous to the subject. In some embodiments, the NK cells are administered systemically. In other embodiments, the NK cells can be administered directly to a tumor site in the subject. In some embodiments, the cancer is selected from the group consisting of a solid tumor, carcinoma, and a hematological malignancy.

BRIEF DESCRIPTION OF DRAWINGS

FIG. 11 illustrates a graphical representation comparing the cytotoxic ability of NK cells generated from the Delta4-bead culture (D4 Bead), NK cells generated from OP9 D4 cells (OP9 D4), and activated peripheral blood NK cells (PB NK) in killing AML cells. Light grey bars represent an Effector:Target ratio of 2:1 (A) or 7:1 (B), dark grey bars represent an Effector:Target ratio of 7:1 (A) or 20:1 (B).

FIG. 12 illustrates a graphical representation comparing the cytotoxic ability of NK cells generated from the Delta4-bead culture (D4 Bead), NK cells generated from OP9 D4 cells (OP9 D4), and activated peripheral blood NK cells (PB NK) in killing AML cells at various Effector:Target ratios.

DETAILED DESCRIPTION

Figure 1C:
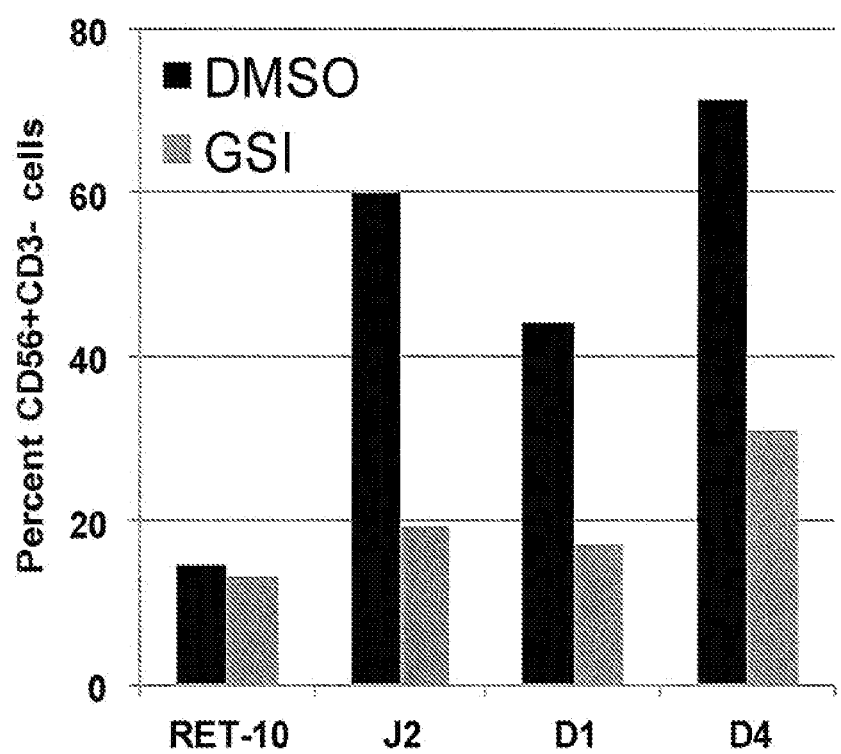
FIG. 1 illustrates that the Notch ligands Jagged2, Delta1, and Delta4 accelerate NK cell differentiation from human CD34+ HPCs. (A) The development of NK cells (defined as CD56+CD3−) from CD34+ HPCs is enhanced by co-culture with OP9 cells expressing Jagged2, Delta1, or Delta4, versus OP9 cells expressing Jagged1 or Delta3 or containing vector (Ret-10) alone. All cultures contain IL-7 and Flt3-L plus IL-15 (black bars) or IL-2 (gray bars). Data shown is from day 21 of co-culture and represents the mean+/− SD of at least 3 experiments. (B) The percentage of Notch-induced NK (N-NK) cells in IL-15+ cultures increases over time and peaks after 4 weeks. Data shown represent the mean+/− SD of at least 3 experiments. (C) NK cell differentiation is inhibited by the presence of a gamma-secretase inhibitor (GSI), L-685, 458, at day 21 of culture. Data shown represents the mean of 2 experiments.

The present invention relates to a method of preparing differentiated natural killer (NK) cells by ex vivo expansion, a substantially homologous cell population of NK cells, and therapeutic methods of using the NK cells generated by the method.

It was found that individual recombinant notch ligands, which are immobilized onto a solid substrate, are capable of inducing expansion and differentiation of functional, inhibitory receptor-negative NK cells from CD34+ hematopoietic cells, with maturation to the level of the stage III NK precursor. The phenotype of notch induced NK cells (N-NK cells) differs slightly, however, from the observed phenotype of stage III NK precursors, which do not express NKp30, NKp46, or NKG2D. In addition, the cytotoxic and cytokine-secreting capabilities of N-NK cells are not characteristic of stage III NK precursors, which do not express perforin, exhibit cytotoxic activity, or secrete IFN-γ. Instead, the functionality of the N-NK cells in conjunction with their immature surface phenotype resembles the "pseudomature" NK cell that develops in vitro in the presence of IL-15; the "pseudomature" term being a reference to the observation that these NK cells have cytotoxic activity yet are CD56bright and negative for KIR.

The notch induced NK cells can also be prepared in absence of stromal cells and even stromal conditioned medium. By providing a method for preparing differentiated NK cells ex vivo from CD34+ hematopoietic cells in the absence of stromal cells or stromal conditioned medium, the present invention provides substantial cost savings to the culturing of such cells, as well as advantageously reducing the likelihood of contamination of such cell cultures by eliminating stromal cells from the cell culture.

Moreover, the observed phenotype and cytotoxic capacity of in vitro-derived N-NK cells show their use as cell therapeutic agents. For example, the allogeneic NK cells can be infused in a subject and used as cell therapy in both solid tumor and hematologic malignancy. A Phase I trial examining the safety of allogeneic NK cell infusion demonstrated the feasibility of this procedure as well as a distinct lack of donor NK cell-mediated graft-versus-host disease (GVHD). The lack of GVHD in this trial is in sharp contrast to the incidence of GVHD following the current clinical practice of donor lymphocyte infusion after hematopoietic stem cell transplantation (HSCT), where significant acute and/or chronic GVHD develops in up to half of treated patients. In addition, data from haploidentical HSCT patients indicate that donor "alloreactive" NK cells, which lack MHC class I inhibitory signals due to KIR:MHC mismatch with recipient cells, can prolong survival in leukemia patients. Mouse models of HSCT demonstrated that alloreactive NK cells may also act as bone marrow conditioning agents and may protect against GVHD by the killing of host dendritic cells.

The cytotoxic activity of N-NK cells against tumor cell lines, which is comparable (though not identical) to activated peripheral blood NK cells, indicates that these cells may act as an anti-tumor agent if infused into patients. NK cell recognition and killing of hematologic malignancy, carcinomas, and neural tumors is dependent in part upon the activating receptors NKG2D, DNAM-1, and/or the natural cytotoxicity receptors, all of which are expressed by N-NK cells. However, N-NK cells would not be capable of antibody-dependent cell-mediated cytotoxicity, which is important in the activity of therapeutic antibodies, since these cells do not express notable levels of CD16. The lack of expression of KIR and NKG2A by N-NK cells shows that these cells are universally alloreactive, i.e. not inhibited by recipient MHC, regardless of HLA type. This results in an ease of administration of such cells, if matching (or, more precisely, mismatching) of donor and recipient HLA is avoided. In addition, because N-NK cells can be derived from CD34+ UCB cells, donor availability and risk are minimal issues, versus the collection of peripheral blood NK cells from adult donors via apheresis.

In accordance with one aspect of the invention, a method of preparing differentiated NK cells by ex vivo expansion includes the step of isolating a plurality of CD34$^+$ hematopoietic cells. In one particular embodiment, the CD34$^+$ hematopoietic cells are obtained and isolated from umbilical cord blood. Conventional techniques for the collection of cord blood may be used. Typically a needle or cannula is used, with the aid of gravity, to drain cord blood from (i.e., exsanguinate) the placenta (Boyse et al., U.S. Pat. No. 5,192,553, issued Mar. 9, 1993; Boyse et al., U.S. Pat. No. 5,004,681, issued Apr. 2, 1991; Anderson, U.S. Pat. No. 5,372,581, entitled Method and apparatus for placental blood collection, issued Dec. 13, 1994; Hessel et al., U.S. Pat. No. 5,415,665, entitled Umbilical cord clamping, cutting, and blood collecting device and method, issued May 16, 1995).

Methods for isolating CD34$^+$ hematopoietic cells are well known to the skilled artisan. For example, a magnetic bead sorting system may be used to isolate CD34$^+$ HPCs from various samples including mononuclear cells (MNCs) from human bone marrow, peripheral blood or umbilical cord blood. In such a system, a superparamagnetic polymer bead coated with a primary monoclonal antibody specific for the CD34 membrane antigen captures the CD34$^+$ cells and then isolates the CD34$^+$ cells using a magnet. The beads can then be removed from the cells leaving a purified population of viable CD34$^+$ hematopoietic cells.

In an exemplary embodiment, once the cord blood has been obtained, CD34$^+$ cells can be isolated from umbilical cord blood MNC's using a CD34$^+$ MACS magnetic bead sorting system (Miltenyi Biotic, Auburn, Calif.). Flow cytometry can then be used to verify the purity of the cells. In some embodiments, the CD34$^+$ cells demonstrate greater than or equal to 97% purity after magnetic bead sorting. The purified cells can then be used fresh or can be cryopreserved for later use in the present methods.

The method further includes the step of culturing the isolated CD34$^+$ cells in medium. According to the present invention, the isolated CD34+ hematopoietic cells are cultured in a medium (e.g., RPMI with 10% FBS and antibiotics) that includes an effective amount of a notch ligand capable of differentiating the CD34$^+$ hematopoietic cells into NK cells. Suitable notch ligands for use in the present invention include Jagged2, Delta1, and Delta4 (Example 1). In one particular embodiment, the notch ligand is Delta4.

Delta4 notch ligand for use in the present invention can be obtained through several well known methods. For example, HEK 293T cells can be transfected using well known standard transfection procedures with a vector encoding a chimeric molecule consisting of extracellular domain of delta4 fused with human IgG1 Fc, termed Delta4:Fc. The presence of the Delta4:Fc chimera in the cell supernatant can be verified using a Western blot and quantified by ELISA using anti-human Fc antibody. The supernatant can then be concentrated if necessary. Delta4:Fc chimera for use in the present invention is also commercially available from Enzo Life Sciences (Farmingdale, N.Y.).

In accordance with the present invention, the recombinant notch ligand is immobilized on a solid substrate that facilitates interaction of the $CD34^+$. The immobilized notch ligand may be immobilized to a variety of immobilization structures including conventional culture vessels, stirring flasks, stirred tank reactors, air lift reactors, suspension cell reactors, cell adsorption reactors and cell entrapment reactors, petri dishes, multi well plates, micro titer plates, test tubes, culture flasks, bags and hollow fiber devices, and cell foam. Such immobilization structures preferably are formed of materials including, for example, polystyrene, polypropylene, acrylate polymers, nylon, cloth, nitrocellulose, agarose, sepharose, and so forth.

Although recombinant notch ligand bound to the bottom of tissue culture wells is capable of inducing NK cell differentiation from $CD34^+$ HPCs, preferred embodiments of the present invention, include the use of a solid substrate which is suspended in the culture medium. It is contemplated that the solid substrate suspended in culture medium will have a greater surface area than a solid substrate fixed or bound to the bottom of a culture well or plate.

Thus, a solid substrate for use in the present invention can include a microbead suspended in the culture medium. In some embodiments, the solid substrate includes a plurality of protein A beads suspended in the culture medium. Exemplary protein A beads for use in the present invention include Dynal Protein A beads (Dynal Biotech, Oslo, Norway). The protein A beads can be coated with chimeric notch ligand described above using well known methods. In one particular example, concentrated supernatant containing Delta4:Fc chimera is combined with protein A microbeads for a target concentration of 40-60 ng Delta4:Fc per µl of beads per manufacturer's instructions. In some embodiments, the amount of Delta4:Fc bound to the beads can be confirmed by ELISA performed on the post-bind supernatant. The notch ligand bound to the solid substrate may then be added to the medium at a concentration of at least about 0.01 µg/ml to about 100 µg/ml. In one particular embodiment, the notch ligand bound to protein A beads can be added to the $CD34^+$ cell culture medium at a concentration of about 0.33 µg/ml.

Preferably, the medium contains an amount of one or more cytolcine(s) effective to induce and direct NK cell differentiation into NK cells, and/or to maintain and expand number of NK cells present in the cell population. The culture medium for preparing differentiated NK cells therefore includes one or more commercially available cytokines typically produced by recombinant DNA techniques. The cytokines are selected from the group consisting of IL-7, IL-15, SCF, Flt-3 and IL-3. In some particular embodiments, the medium also includes IL-6. In one exemplary embodiment, Delta4:Fc coated protein A microbeads are incubated/cultured with CD34+ cells in the presence of IL-7, SCF, Flt-3, IL-3, IL-15 and IL-6. It may be advantageous to change half of the media in the culture twice weekly, with addition of fresh cytokines.

The present invention is not limited by the amount or concentration of cytokines added to the medium. It is well within the ability of the skilled artisan to select a suitable amount of one or more cytokine for use in the present invention. The amount of cytokines used in the medium depends on the activity of the cytokine preparation and on the combination of cytokines used. Typically, concentrations range from about 0.5 ng/ml to about 500 ng/ml. The optimum concentration of each growth factor has to be determined for individual culture conditions since some growth factors act synergistically with other growth factors.

The method further includes the step of maintaining the $CD34^+$ cells in the culture described above for a duration of time sufficient to produce differentiated NK cells. In some embodiments, differentiated NK cells may be detected in culture as early as day 14, however the NK cells may cease to proliferate after week 6. In general, the determination of an increase in the number of NK cells and/or their state of differentiation is assessed using conventional methods known to those of ordinary skill in the art. For example, the cultured cells may be monitored by flow cytometry for the development of NK cells by staining the cells with anti-CD56 and anti-CD3 antibodies. Cells which are $CD56^+/CD3^-$ would be indicative of differentiated NK cells.

In addition to inducing NK cell differentiation, it is contemplated by the present invention that Notch signaling also causes marked expansion of total NK cell number. In general, expanding the number of differentiated NK cells refers to increasing the number of cells in culture by at least approximately 2-fold relative to the number of cells that are present when the $CD34^+$ cells initially are cultured in the differentiating medium or to a negative control culture. In some embodiments, the number of cells in culture are increased at least approximately 10-fold, 20-fold or even at least 100-fold relative to the number of cells that are present when the $CD34^+$ cells are initially placed in the differentiating medium.

As described above, a negative control culture may be used to determine the effectiveness of the differentiation and expansion of the NK cells. For example, a commercially available non-notch ligand chimera (e.g., CD14:Fc) may be bound to protein A microbeads and incubated with $CD34^+$ cells to serve as a negative control.

After the cells are cultured for an amount of time sufficient to produce differentiated NK cells, the resultant differentiated/expanded NK cells are immature but functional NK cells resembling, but distinct from, immature $CD56^{bright}$ NK cells found naturally in the human body. The inventive NK cells are marked by the ability to secrete cytokines such as IFN-γ and cytotoxic granules containing perforin and granzymes, which promote target cell death. The differentiated NK cells also express activating NK cell receptors important for tumor cell recognition and killing, while at the same time the inventive NK cells lack a majority of NK cell inhibitory receptors.

In humans, NK cells are regulated by clonally distributed killer immunoglobulinlike receptors (KIRs) that recognize allotypic determinants displayed by different human leucocyte antigen (HLA) class I alleles. Inhibitory KIRs are generally dominant and prevent NK cells from killing autologous cells. As shown in the Examples below, the differentiated NK cells prepared by the present method lack MHC class I inhibitory signals (e.g., KIR and NKG2A).

The receptor phenotype of NK cells prepared by the present method further includes expression of the natural cytotoxicity receptors (NKp30, NKp44, NKp46) and CD244 (2B4) while having low expression of NKG2D. The resultant NK cells of the present invention can further be identified by the following receptor phenotype: $CD56^{bright}$, CD16−, $CD117^+$, KIR−, $CD94^{low}$, CD11b−.

The phenotype of the NK cells of the present invention are similar to, but distinct from, the NK cells described in Example 1 below, which are cultured with notch ligand-expressing OP-9 stromal cells. The NK cells co-cultured with stromal cells are DNAX accessory molecule-1 (DNAM-1) positive while the NK cells prepared by the method of the present invention, lack DNAM-1 expression.

The differentiated NK cells of the present invention are further identified by their capability to lyse various hematopoietic tumor cells lines (e.g., human acute myeloma leukemia lines K562 and OCI-AML3, and the human myeloma cell line RPMI-8226) at levels similar to activated peripheral blood NK cells. The cytotoxic capabilities of the cells in culture can therefore be measured to verify the differentiated NK cell phenotype prepared by the inventive method. The ability of the differentiated NK cells to lyse hematopoietic tumor cell lines can be measured using well known release assays (e.g., chromium-51(Cr51) release assay europium (Eu) release assay, and sulfur-35 (S35) release assay), where target cell lysis is measured by release of a radioactive intracellular label by a scintillation counter. In some embodiments however, the lysing ability can be examined using a commercially available non-radioactive cytotoxicity assay Cyto Tox-Glo (Promega, Madison, Wis.).

As described herein, the differentiated NK cells of the present invention represent a previously unidentified NK cell population with a unique identifiable cellular phenotype. Therefore, the present invention also relates to a substantially homogenous cell population of NK cells prepared by culturing CD34+ cells in medium including an effective amount of notch ligand immobilized on a solid substrate and one or more cytokines selected from the group consisting of IL-7, IL-15, SCF, Flt-3, IL-3, and IL-6. In some embodiments, the percentage of NK cells in the homogenous cell population is greater than about 60%. In some embodiments, the percentage of NK cells is greater than about 70%. In other embodiments, the percentage of NK cells is greater than about 80%. In still other embodiments, the percentage of NK cells is greater than about 90%. As shown in the examples below, most of the remaining non-NK cells are CD33+ myeloid cells.

As described above, the inventive NK cells have both cytokine-secreting and cytotoxic functions. The inventive NK cells also express activating NK cell receptors important for tumor cell recognition and killing. Moreover, the inventive NK cells lack a majority of mature NK cell inhibitory receptors. The cytotoxic activity of the inventive NK cells against tumor cell lines described herein, which is comparable (though not identical) to activated peripheral blood NK cells, indicates that these cells can act as an anti-tumor agent if administered to a subject.

NK cell recognition and killing of hematologic malignancy, carcinomas, and neural tumors is dependent in part upon the activating receptors (e.g., NKG2D) and the natural cytotoxicity receptors, expressed by the inventive NK cells. It is further contemplated that the phenotype and functionality of the NK cells produced by the present invention can be utilized in cellular therapies for the treatment of malignancies. Thus, methods of the present invention could be used to generate large numbers of functional differentiated NK cells for cell therapy purposes.

The lack of expression of KIR and NKG2A by the inventive NK cells indicates that these cells can be universally alloreactive, i.e., not inhibited by recipient MHC, regardless of HLA type. Overcoming the inhibitory signals transmitted by MHC-recognizing receptors is an important stratagem in the use of cytotoxic NK cells as a therapy against different types of malignancy. (Ljunggren et al. Nat Rev Immunol 2007; 7:329-339). Furthermore, the use of Notch ligands to generate large numbers of functional, inhibitory receptor-negative NK cells has been described as useful for producing human NK cells for cell therapy purposes, as infusion of allogeneic NK cells is one strategy for tumor immunotherapy (Ljunggren et al. (2007); Miller et al. Blood 2005; 105:3051-3057). It has also known that in hematopoietic transplants, when the recipient's class I alleles do not block all donor NK cells, donor alloreactive NK clones are generated, which kill host targets, including acute myeloid leukemia (AML) cells (L. Ruggeri et al., Blood 94, 333 (1999)).

Therefore, the present invention also relates to a method of treating cancer in a subject. The method includes the step of administering to the subject a therapeutically effective amount of a substantially homogenous population of differentiated NK cells. In some embodiments, the NK cells are autologous to the subject. In other embodiments, the NK cells are allogeneic to the subject. Exemplary cancers treated by the present invention include solid tumors, carcinomas, and hematological malignancies (e.g., leukemia and myeloma).

Figure 4:
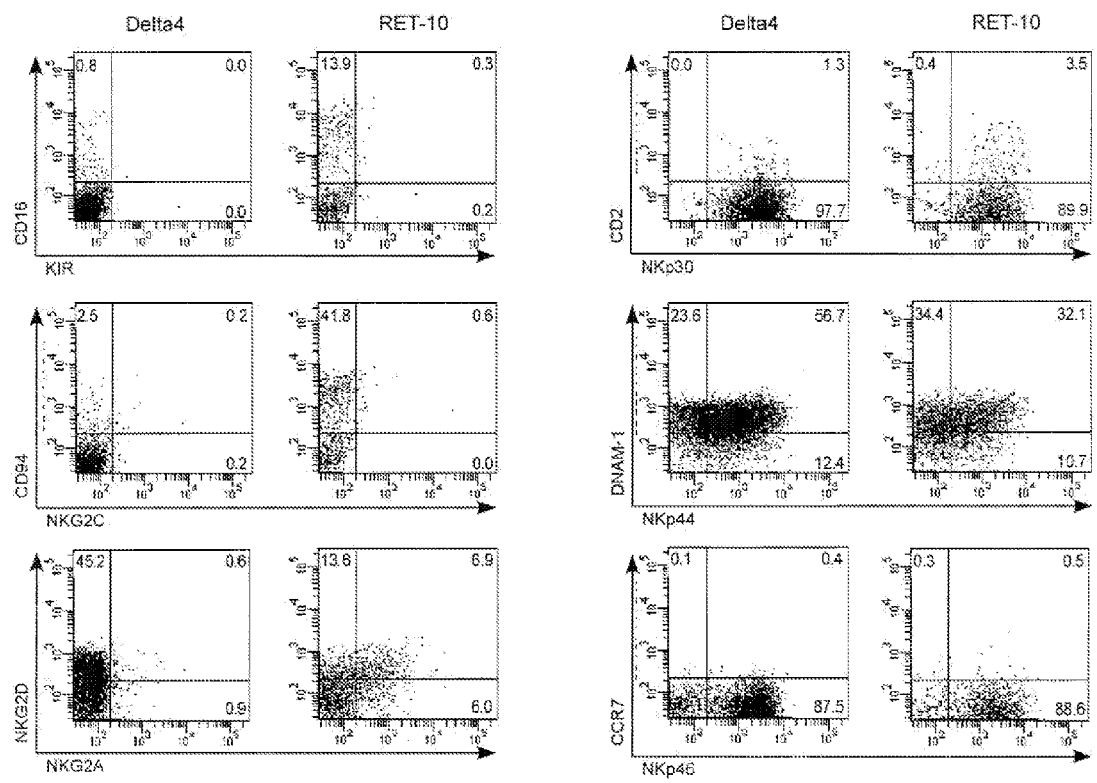
FIG. 4 illustrates that N-NK cells have a predominantly immature NK cell surface phenotype but do express NKG2D and the natural cytotoxicity receptors, NKp30, NKp44, and NKp46. Expression of NK cell markers was examined on gated $CD56^+CD3$-cells from 4 week-old co-cultures containing Delta4 or no Notch ligand (RET-10). KIR expression was examined by an antibody cocktail (DX9+CD158a+CD158b). Data from cultures containing the Notch ligands Jagged2 or Delta1 showed similar results to the Delta4 culture. Data shown is representative of at least 4 independent experiments.

The inventive NK cells can also be used to treat GVHD in subjects who have received an allogeneic transplant. It is well known that protection against GVHD can be mediated by alloreactive NK cells attacking recipient antigen-presenting cells (APCs), shown to be responsible for initiating GVHD (H. Kosaka et al. Exp. Med. 176,1291 (1992); W. D. Slomchik et al., Science 285, 412 (1999)). It has been further shown by the inventors that alloreactive NK cells administered to a subject, accelerated the loss of bone marrow, spleen, and gut APCs (FIG. 4, B, through D). Mouse models of hematopoietic stem cells transplant have also demonstrated that alloreactive NK cells can act as bone marrow conditioning agents and protect against GVHD by the killing of host dendritic cells (L. Ruggeri et al. Science 2002; 295:2097-2100).

Taken together, these data indicate that alloreactive NK cells prevent GVHD by elimination of recipient APCs. Thus, it is further contemplated that the NK cells of the present invention have specific cytotoxic activity towards a host's antigen presenting cells, thereby inhibiting GVHD in the subject following HPC transplantation. Therefore, the present invention also relates to a method of treating cancer in a subject by administering to the subject a therapeutically effective amount of hematopoietic precursor cells and a substantially homogenous cell population of differentiated NK cells.

It is further contemplated that the inventive NK cells' ability to treat or prevent GVHD could allow a greater T cell content in the graft and consequently reduce the infection-related morbidity and mortality that are associated with extensive T cell depletion (F. Aversa et al., Blood 84, 3948 (1994), F. Aversa et al., N. Engl. J. Med. 339, 1186 (1998)).

The HPCs for use in the present method can be derived either from the cancer patient (autologous transplant) or from a histocompatible donor (allogeneic donor). The HPCs administered to the subject can be isolated from bone marrow, peripheral blood or from umbilical cord blood. In general, the cells are harvested before chemotherapy or radiation therapy.

The differentiated NK cells administered to the subject are typically harvested and washed with fresh culture medium before infusion to the patient. In some embodiments, the NK cells can be administered systemically. In other embodiments, the NK cells can be administered directly to a tumor site in the subject or as desired by a practitioner. The NK cells may be administered concurrently with the HPCs or may be administered at a different time.

As used herein, the term "therapeutically effective amount" refers to that amount of differentiated NK cells that relieves to some extent one or more symptoms of a disease (such as a cancer or GVHD related to transplantation), or returns to normal, either partially or completely, one or more physiological or biochemical parameters associated with or causative of the disease, decreased cancer growth, amelioration of symptoms, and/or a prolongation of survival in a subject.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it; (b) inhibiting the disease, i.e., arresting its development; and (c) relieving the disease, i.e., causing regression of the disease.

The following example is for the purpose of illustration only and is not intended to limit the scope of the claims, which are appended hereto.

EXAMPLES

Example 1

To further define the capacity of Notch ligands to modulate development of human NK cells, we determined the differential ability of the 5 different Notch ligands found in vertebrates to induce NK cell differentiation and expansion from $CD34^+$ HPCs isolated from umbilical cord blood (UCB). In addition, we analyzed the cell surface phenotype and function of Notch-induced NK (N-NK) cells and compared these characteristics to NK cells generated in vitro in the absence of Notch signaling, as well as to NK cells found in normal adult peripheral blood. N-NK cells display a predominantly immature CD56bright surface phenotype, with no expression of CD16, and the capacity to secrete IFN-γ. Unlike physiologic CD56bright NK cells, however, they do not express CD94 and have only moderate levels of NKG2D expression. In addition, N-NK cells lack the inhibitory receptors NKG2A and KIRs, yet they do express all three of the NCRs, NK-30, NKp44, and NKp46, and are able to lyse hematopoietic tumor cell lines in vitro. Thus, the receptor profile of N-NK cells is biased toward activating NK cell receptors. Finally, the presence of Notch ligand stimulates marked expansion of NK cells from HPCs, resulting in average yields of 700 to 1100 NK cells per input cell.

Elucidation of the ability of different Notch ligands to induce NK cell differentiation and expansion, as well as evidence for the functionality of N-NK cells, allow for more optimal design of in vitro NK cell culture strategies for cell therapy.

OP9 Cell Lines

The murine bone marrow stromal cell line OP9 (Nakano T, Kodama H, Honjo T. Generation of lymphohematopoietic cells from embryonic stem cells in culture. Science 1994; 265:1098-1101) was transduced with one of five different Notch ligands in a bicistronic message with green fluorescent protein (GFP) in the vector Ret-10, to generate the lines OP9-Jagged1, OP9-Jagged2, OP9-Delta1, OP9-Delta3, and OP9-Delta4, as previously described. (Zhou L, Li L W, Yan Q, et al. Notch-dependent control of myelopoiesis is regulated by fucosylation. Blood 2008; 112:308-319) A control cell line, OP9-Ret-10, was transduced with vector containing GFP alone. The OP9 cell lines were maintained in α-MEM with 20% FBS and antibiotics.

Human Cells and OP9 Co-Culture

Peripheral blood was obtained from healthy volunteers via the Stem Cell Core Facility of the Case Comprehensive Cancer Center via IRB-approved protocols, and NK cells were isolated from the mononuclear cell (MNC) fraction using a negative selection kit from Miltenyi Biotec (Bergisch Gladbach, Germany). For isolation of $CD34^+$ HPCs, UCB units were obtained from the labor and delivery unit at University Hospitals Case Medical Center under an IRB-approved protocol. After ficoll gradient, CD34+ cells were isolated from UCB MNCs using the CD34 MACS system from Miltenyi Biotec. Flow cytometric analysis of purified CD34+ cells routinely demonstrated ≧97% purity. $CD34^+$ cells were used fresh or cryopreserved for later use.

For co-culture, $2 \times 10^4$ OP9 cells were seeded per well in 12-well plates and allowed to adhere at least 4 hours at 37° C., after which time $2-2.5 \times 10^4$ $CD34^+$ UCB HPCs were plated onto the OP9 cells in RPMI supplemented with 10% FBS and antibiotics. Cells were cultured in the presence of recombinant cytokines: hIL-7 (10 ng/ml), hFlt3 ligand (10 ng/ml), and hIL-15 (10 ng/ml). In some initial experiments, hIL-2 (25 ng/ml) was used in place of hIL-15. When indicated, cultures were further stimulated with hIL-12 and hIL-18, both used at 100 ng/ml. All cytokines were purchased from R&D Systems (Minneapolis, Minn.). Half of the media in the co-culture wells was changed twice weekly, with addition of fresh cytokines. To prevent OP9 overgrowth, HPCs were transferred to fresh OP9 monolayers weekly. After two weeks of co-culture, the hematopoietic cells were split in half onto new OP9 monolayers at least weekly, to prevent overcrowding. Some co-cultures were plated and cultured in the presence of 10 μm of the γ-secretase inhibitor, L-685,458 (Sigma Aldrich, St. Louis, Mo.) dissolved in DMSO (Blood 2008; 112:308-319).

Flow Cytometry

Cells were harvested from co-culture at indicated time points and were treated with human FcR blocking reagent (Miltenyi Biotec) prior to antibody staining. The following anti-human antibodies were used for analysis: CD1a-PE, CD2-FITC, CD3-FITC, CD7-FITC, CD11b (MAC-1)-FITC, CD11c-FITC, CD16-FITC or -PE, CD18-FITC, CD19-FITC, CD33-PE, CD56-FITC or -PE or -APC, CD62L (L-selectin)-PE, CD94-FITC, CD 117-PE, CD 181 (CXCR1)-FITC, CD244 (2B4)-PE, CD226 (DNAM-1)-FITC, CD314 (NKG2D)-FITC or -PE, ICAM-1-PE, and perforin (eBioscience, San Diego, Calif.); CD335 (NKp46)-PE, CD336 (NKp44)-PE, and CD337 (NKp30)-PE (Miltenyi Biotec); CD11a (LFA-1)-PE, NKG2A-PE, and NKG2C-PE (R&D Systems); CD158a-PE and CD158b-PE (Immunotech Beckman Coulter, Marseille, France); DX9 (BD Pharmingen, San Jose, Calif.). KIR expression was determined by combining the CD158a, CD158b, and DX9 antibodies, which combination will detect KIR2DL1/2/3, KIR2DS1/2/4, and KIR3DL1. (Miller J S, McCullar V. Human natural killer cells with polyclonal lectin and immunoglobulinlike receptors develop from single hematopoietic stem cells with preferential expression of NKG2A and KIR2DL2/L3/S2. Blood 2001; 98:705-713). For analysis of perforin expression, cells were fixed and permeabilized using FIX & PERM® (Invitrogen, Carlsbad, Calif.) according to manufacturer's protocol and stained with perforin and CD56 antibodies. Three color (FITC, PE, propidium iodide [PI]) analysis was performed on a FACScan machine (Becton Dickinson, Franklin Lakes, N.J.) and analyzed with the manufacturer's CellQuest software. Alternatively, four color (FITC, PE, PI, APC) analysis was performed using a FACSAria (Becton Dickinson) and analyzed using BD's FACScalibur software. All analysis used forward and side scatter gating to exclude OP9 cells and PI exclusion to gate on live cells.

Cytotoxicity Assays and Inhibition of Perforin

The Cytotox 96® non-radioactive cytotoxicity assay (Promega, Madison Wis.) measures LDH release by colorimetric methods. After 3 or 4 weeks of co-culture, harvested cells were analyzed for percent CD56+CD3− (effector, E) cells by flow cytometry. For cells derived in the absence of Notch ligand, due to the low level of CD56+CD3− cells, NK cell enrichment was performed via negative selection using anti-CD13 antibody (eBioscience) and goat-anti mouse IgG magnetic beads (Miltenyi Biotec). Effector cells were plated in triplicate in 96-well round-bottom plates with 1 or $1.5 \times 10^4$ target (T) cells at indicated E:T ratios. After 4 hours at 37° C., plates were centrifuged and supernatant was collected and assayed for LDH release according to manufacturer protocol. Percent specific lysis was calculated using averaged absorbance values: [(experimental−E spontaneous−T spontaneous)/(T maximum−T spontaneous)]×100. The following human hematopoietic cell lines were used as target cells: Daudi, Jurkat, RPMI-8226, and U266 (American Type Culture Collection, Manassas, Va.); Jurkat, HL-60 (kind gifts of Dr. Stanton Gerson); K562 (kind gift of Dr. Clifford Harding).

For inhibition of perforin, E cells were pre-treated with either concanamycin-A (Sigma Aldrich) dissolved in DMSO at indicated concentrations or DMSO for 1 hour at 37° C., then washed twice before use in the cytoxicity assay.

IFN-µ ELISA

Supernatants were collected from co-cultures and analyzed for the presence of IFN-µ using a standard sandwich ELISA containing capture and detection antibodies from eBioscience.

The Notch Ligands Jagged2, Delta1, and Delta4 Induce CD56+CD3-Cells from Human HPCs To determine whether Notch ligands are able to generate NK cells from human HPCs, we used a bone marrow stromal cell line, OP9, transduced with each of the individual Notch ligands (Jagged1, J1; Jagged2, J2; Delta1, D1; Delta3, D3; Delta4, D4) in a bicistronic message with GFP, resulting in the lines OP9-J1, OP9-J2, OP9-D1, OP9-D3, and OP9-D4. (*Blood* 2008; 112:308-319). A control cell line, OP9-Ret-10, contained vector having only the GFP sequence. Expression of transduced Notch ligand by each OP9 line was proportional to the expression of GFP, and flow cytometric analysis demonstrated a range of green fluorescence intensity from 0.9- to 2.5-fold versus OP9-Ret-10. CD34+ cells isolated from umbilical cord blood were cultured with each cell line, in the presence of IL-7, Flt3L, and IL-15. After 21 days in culture, the Notch ligands Jagged2, Delta1, and Delta4 demonstrated the greatest capacity for inducing NK cell development, as measured by percent CD56+CD3-cells in the culture (FIG. 1A), with Jagged2 producing an average of 76% NK cells, Delta1, 67%, and Delta4, 70% NK cells in the presence of IL-15. The non-NK cells in the cultures containing Jagged2, Delta1, and Delta4 consisted of $CD33^+$ myeloid cells and $CD7^+CD1a$-lymphoid precursors, presumed to be NK cell precursors due to the lack of CD1a expression (FIG. 2). In contrast, in the absence of IL-15, Notch signaling via Jagged2, Delta1, and Delta4 drove the development of T cell precursors, defined as being positive for both CD7 and CD1a (FIG. 2A and data not shown), in agreement with prior observations (La Motte-Mohs R N, Herer E, Zuniga-Pflucker J C. Induction of T-cell development from human cord blood hematopoietic stem cells by Delta-like 1 in vitro. *Blood* 2005; 105:1431-1439) and with the established role for Notch signaling in T cell development. Cultures containing Jagged1 or Delta3 or without Notch ligand in the presence of IL-15 consistently produced less than 25% CD56+CD3− cells at day 21 of culture; these cultures consisted predominantly of CD33+ cells (FIG. 2 and data not shown). Similar results for each Notch ligand were seen when IL-2 was used in culture instead of IL-15 (FIG. 1 and data not shown). For the remainder of the experiments, IL-15 was used to drive NK cell differentiation in the co-cultures.

Figure 2:
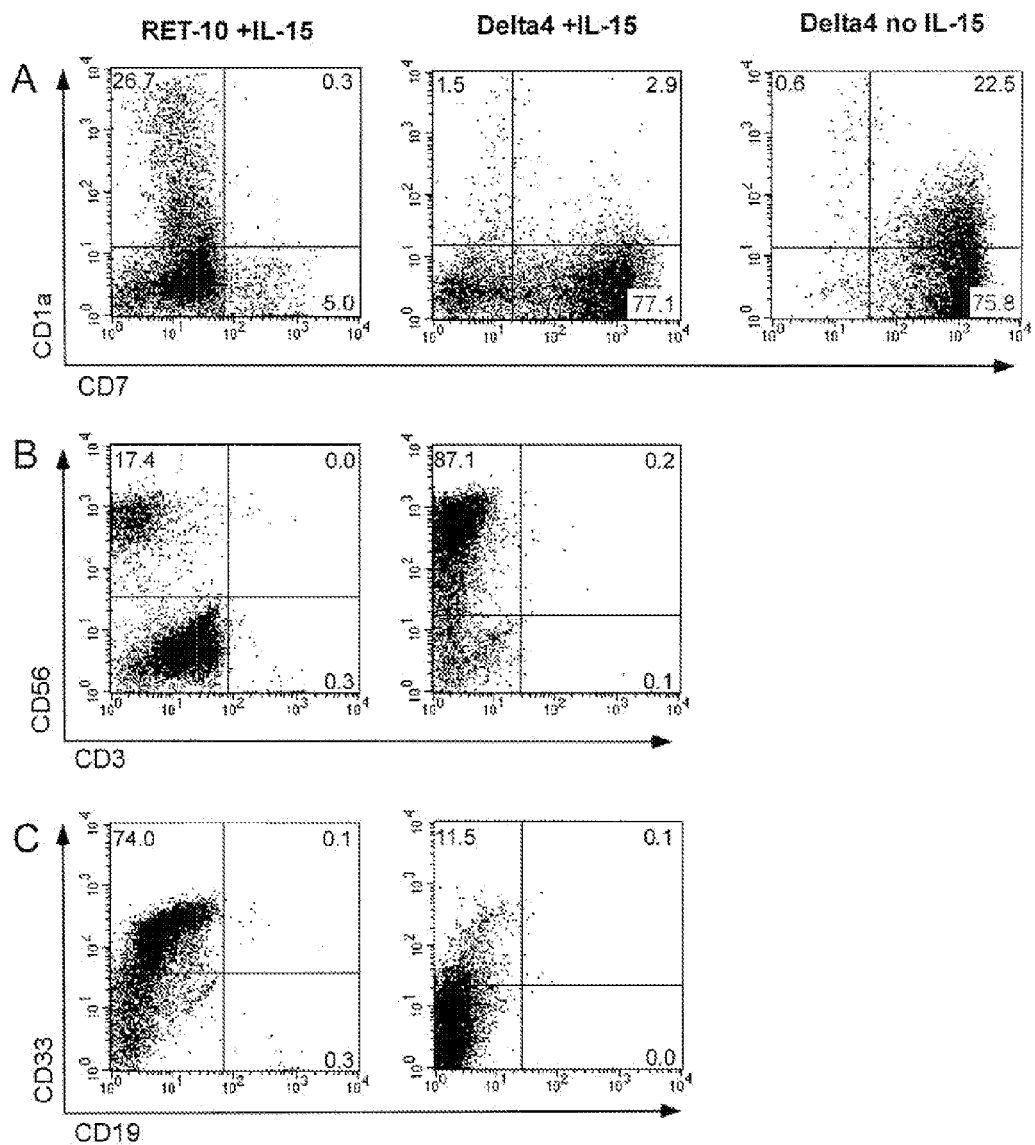
FIG. 2 illustrates that a culture of CD34+ HPCs in the presence of IL-15 and Notch ligand drives NK cell differentiation, without T or B cell maturation. Flow cytometric analysis of 4 week-old cultures containing the Notch ligand Delta4 and IL-15 demonstrate abundance of $CD7^+CD56^+$ NK cells and no T cell precursors (A), mature T cells (CD3+; B), or B cells ($CD19^+$; C), while culture without IL-15 in the presence of Delta4 demonstrates predicted T cell precursors ($CD1a^+CD7^+$; A). Culture without Notch ligand (RET-10) in the presence of IL-15 demonstrates few $CD7^+$ NK cell precursors and $CD56^+$ NK cells (A, B), with mostly $CD33^+$ myeloid cells and no development of T or B cells (A-C). All cultures contained IL-7 and FltL. Data from cultures containing the Notch ligands Jagged2 or Delta1 showed similar results to the Delta4 culture. Data shown is representative of at least 4 experiments.

The appearance of NK cells could be seen as early as day 14 in culture (FIG. 1B) and continued to rise until day 28, at which time NK cells became 80-90% of total hematopoietic cells in co-cultures containing Jagged2, Delta1, or Delta4 (FIG. 1C). The NK cells continued to dominate cultures by day 42, but proliferation decreased after day 28, and the cultures ceased to proliferate between days 35-42 (data not shown). No $CD19^+$ or $CD3^+$ cells were seen in any culture condition at any time point (FIG. 2). The induction of $CD56^+$ CD3− by Jagged2, Delta1, or Delta4 was dependent on signaling via the Notch receptor, as the level of NK cell differentiation was greatly reduced in the presence of a gamma-secretase inhibitor (GSI), an inhibitor of Notch signaling (FIG. 1B). The presence of the GSI, however, failed to abrogate NK cell differentiation in cultures containing OP9-Ret-10, indicating that the development of NK cells in these cultures was not dependent on Notch signaling.

Figure 3:
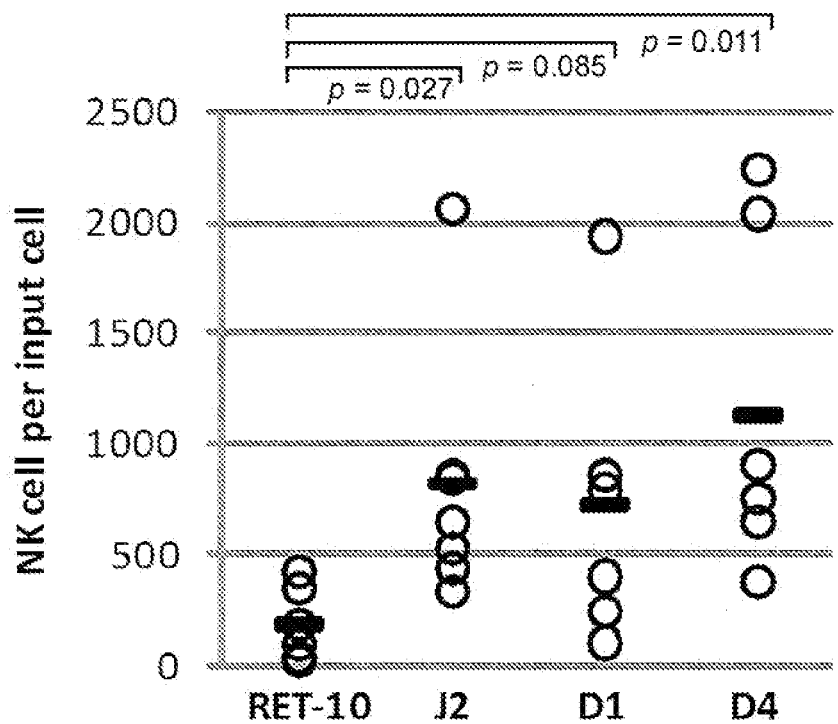
FIG. 3 illustrates that the Notch ligands Jagged2, Delta1, and Delta4 induce NK cell expansion from human $CD34^+$ HPCs. The number of NK cells (defined as $CD56^+CD3^−$) derived per single $CD34^+$ input cell at day 28 of culture in the presence of IL-15 is shown; each symbol represents an individual experiment with the horizontal bar indicating the mean (n=5-7 independent experiments). P values generated by student's t-test are shown.

In addition to inducing NK cell differentiation, Notch signaling via ligation with Jagged2, Delta1, or Delta4 also caused marked expansion of total NK cell number, resulting in average yields of 700 (Delta1), 800 (Jagged2), or 1100 (Delta4) NK cells per input cell on day 28 of culture, versus an average yield of 200 NK cells per input cell in the absence of Notch ligand (FIG. 3).

TABLE 1

Surface phenotype of Notch-induced NK cells (day 28 of culture), as compared to NK cells developed in the absence of Notch and normal peripheral blood NK cells.*

|  | OP9-J2 | OP9-D1 | OP9-D4 | OP9-Ret-10 | PB NK |
|---|---|---|---|---|---|
|  | Markers of NK cell maturity/lineage | | | | |
| CD16 | 3.3 ± 3.6 | 3.4 ± 1.7 | 3.8 ± 2.0 | 30.1 ± 9.8 | 97.1 ± 2.3 |
| CD94 | 8.4 ± 3.7 | 15.6 ± 8.3 | 10.1 ± 10.2 | 51.6 ± 10.0 | 76.1 ± 12.0 |
| CD117 | 94.8 ± 9.5 | 90.1 ± 11.2 | 91.2 ± 15.0 | 21.3 ± 25.1 | 5.9 ± 6.2 |
| CD11b | 21.9 ± 13.0 | 18.7 ± 10.7 | 20.4 ± 9.5 | 68.2 ± 10.7 | 97.2 ± 1.5 |
| CD2 | 4.3 ± 6.0 | 4.3 ± 4.0 | 5.5 ± 5.7 | 8.8 ± 4.2 | 80.8 ± 0.9 |
| CD7 | 56.5 ± 12.8 | 57.1 ± 8.9 | 74.2 ± 9.5 | 25.6 ± 6.2 | 98.8 ± 1.1 |
| DNAM-1 | 55.9 ± 18.6 | 39.6 ± 24.0 | 67.0 ± 15.0 | 73.8 ± 12.1 | 84.2 ± 14.7 |
| 2B4 | 99.3 ± 1.3 | 97.9 ± 2.6 | 99.4 ± 0.8 | 91.4 ± 7.0 | 99.9 ± 0.2 |

TABLE 1-continued

Surface phenotype of Notch-induced NK cells (day 28 of culture), as compared to NK cells developed in the absence of Notch and normal peripheral blood NK cells.*

|  | OP9-J2 | OP9-D1 | OP9-D4 | OP9-Ret-10 | PB NK |
|---|---|---|---|---|---|
| Inhibitory NK receptors | | | | | |
| NKG2A | 1.6 ± 0.8 | 1.9 ± 1.2 | 2.4 ± 2.2 | 14.5 ± 6.4 | 23.2 ± 23.6 |
| KIR§ | 0.1 ± 0.1 | 0.2 ± 0.4 | 0.0 ± 0.0 | 0.4 ± 0.2 | 68.7 ± 15.4 |
| Activating NK receptors | | | | | |
| NKG2C | 0.2 ± 0.3 | 0.3 ± 0.2 | 0.1 ± 0.1 | 1.4 ± 1.8 | 19.2 ± 26.6 |
| NKG2D | 31.2 ± 17.8 | 17.9 ± 15.0 | 33.6 ± 26.5 | 45.1 ± 11.6 | 54.1 ± 1.8 |
| NKp30 | 80.8 ± 21.4 | 76.3 ± 23.9 | 65.2 ± 24.5 | 81.4 ± 7.2 | 91.5 ± 13.9 |
| NKp44 | 47.8 ± 11.5 | 40.2 ± 11.9 | 56.1 ± 15.0 | 21.9 ± 10.4 | 0.8 ± 1.1 |
| NKp46 | 94.5 ± 5.1 | 90.4 ± 3.8 | 93.3 ± 7.5 | 92.2 ± 2.2 | 82.4 ± 22.6 |
| Adhesion molecules | | | | | |
| CCR7 | 3.7 ± 2.9 | 2.5 ± 1.6 | 2.7 ± 1.2 | 3.2 ± 0.7 | 0.1 ± 0.1 |
| CXCR1 | 1.9 ± 2.8 | 1.7 ± 1.4 | 1.3 ± 1.0 | 2.5 ± 1.0 | 71.9 ± 5.5 |
| CD62L | 52.7 ± 13.1 | 61.6 ± 11.4 | 67.2 ± 19.8 | 75.0 ± 6.5 | 60.1 ± 23.5 |
| ICAM-1 | 97.0 ± 3.1 | 96.1 ± 3.8 | 95.1 ± 3.6 | 97.7 ± 1.3 | 97.2 ± 0.1 |
| CD11a | 55.1 ± 23.5 | 52.2 ± 23.8 | 65.3 ± 21.7 | 71.2 ± 9.6 | 73.6 ± 17.8 |
| CD18 | 83.7 ± 9.1 | 77.1 ± 8.4 | 78.8 ± 13.6 | 98.1 ± 0.8 | 100.0 ± 0.0 |

*Numbers indicate percentage of CD56+CD3− cells positive for that antigen and are expressed as the mean of 3 experiments using OP9 cells, +/− standard deviation.
Data for PB NK is derived from 3 normal donors.
§Antibodies used also detect the activating receptors KIR2DS1, KIR2DS2, and KIR2DS4.

The Surface Phenotype of N-NK Cells Resembles, but is Distinct from, that of Immature (CD56$^{bright}$) NK Cells.

We next determined the maturation stage of N-NK cells by surface receptor expression. Flow cytometric immunophenotyping was performed on the NK cells in cultures containing Jagged2, Delta1, or Delta4, and compared to that of NK cells developed in the absence of Notch signaling or normal peripheral blood NK cells (Table 1). N-NK cells had a predominantly immature NK cell phenotype, with bright expression of CD56, expression of CD117 and CD7, and very little, if any, expression of CD16, CD94, and KIRs (FIGS. 2 and 4). The lack of CD94 expression corresponded to an absence of detectable NKG2A and NKG2C expression (FIG. 4), both of which form heterodimers with CD94 to form receptors that mediate inhibitor signals upon binding to HLA-E expressed by target cells. Interestingly, N-NK cells expressed moderate levels of the activating receptor NKG2D and high levels of the NCRs NKp30, NKp44, and NKp46 (FIG. 4). This was in contrast to NK cells found in peripheral blood, which expressed only NKp30 and NKp46, and NK cells developed in vitro in the absence of Notch ligand, which expressed low levels of NKp44 (Table 1). NKp44 is an activation-induced receptor, and the high expression of all three NCRs on N-NK cells may indicate an activated state of these cells. Interestingly, CCR7 was not expressed by N-NK cells, although the adhesion ligands CD62L, CD11a, and CD18 were (Table 1). N-NK cells also failed to express high levels of CXCR1 and CD11b (Mac-1), markers of mature, CD56dim peripheral blood NK cells.

Both N-NK cells and NK cells derived in the absence of Notch ligand have bright CD56 expression and lack expression of more mature NK cell markers (such as CD16, CD94, KIR, and Mac-1). However, the NK cells derived in the absence of Notch ligand differed from N-NK cells, having higher levels of CD94 and NKG2A and lower levels of CD11. These results are consistent with a more mature phenotype, similar to that described in published in vitro models of NK cell development using CD34+ cord blood HPCs cultured with stromal cells. Thus, the overall phenotype of N-NK cells is distinct from any previously described in vitro or in vivo NK cell subset.

N-NK Cells Have Cytotoxic Capacity and Can Secrete IFN-γ

Figure 5:
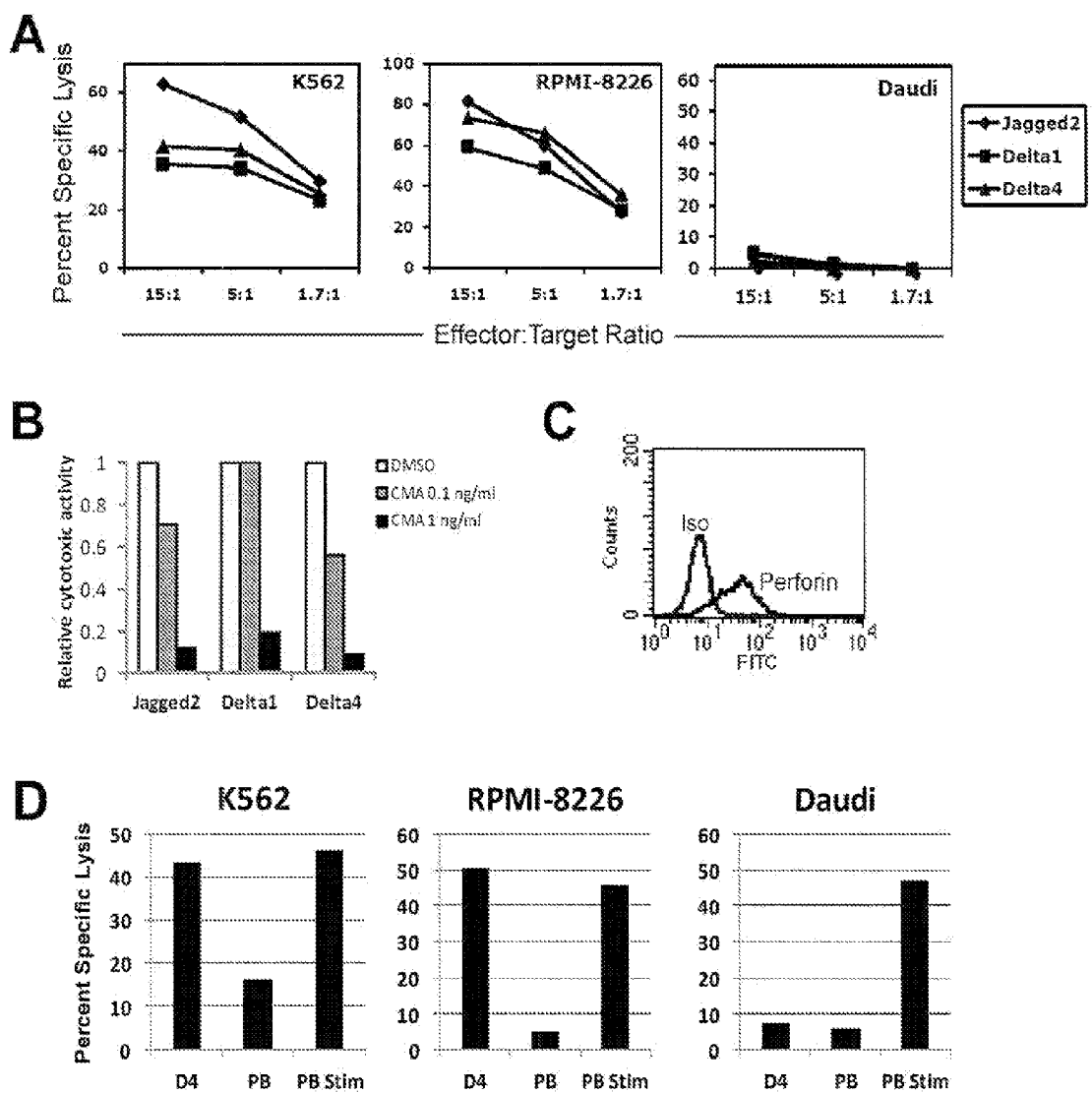
FIG. 5 illustrates that N-NK cells have perforin-dependent cytotoxic activity. (A) Cytotoxicity assays demonstrate activity against the human leukemia cell lines K562 and RPMI-8226 but not Daudi. N-NK cells from week 3 or 4 of co-culture were used as effector cells. (B) N-NK cell cytotoxicity assay against K562 cells is abrogated in the presence of the perforin inhibitor concanamycin-A (CMA). The Effector: Target ratio is 10:1. (C) N-NK cells from week 4 of Delta4 co-culture express perforin by flow cytometry; N-NK cells from Jagged2 and Delta1 cultures have similar levels of perforin expression (not shown). (D) The level of cytotoxic activity of Delta4-derived N-NK cells is similar, but not identical, to activated PB NK cells (PB Stim), and is greater than unstimulated PB NK cells (PB). PB NK cells were activated by overnight incubation with IL-15 (10 ng/ml). Averages of 3 independent experiments are shown.

Among normal human NK cell subsets, the CD56dim population has more cytotoxic activity than the CD56bright population, while CD56bright cells play an important role in secretion of IFN-γ and other inflammatory cytokines. In contrast to the immature surface phenotype observed for N-NK cells, we consistently noticed that N-NK cells began to lyse the OP9 stromal cells during the third week of co-culture, indicating the presence of cytolytic capability. To directly demonstrate the functional capacity of N-NK cells, cytotoxicity was measured by in vitro assays using the human hematopoietic tumor cell lines K562 (erythroleukemia), RPMI-8226 (multiple myeloma), and Daudi (Burkitt lymphoma; FIG. 5A). N-NK cells derived from Notch signaling via Jagged2, Delta1, and Delta4 demonstrated similar levels of cytotoxicity. RPMI-8226 cells express high levels of surface MHC class I molecules, while K562 and Daudi do not (data not shown), indicating that the cytotoxic activity of N-NK cells is not inhibited by tumor cell expression of MHC class I. This is not surprising, given the absence of KIR and CD94/NKG2A and CD94/NKG2D expression by N-NK cells. The cytotoxic ability of N-NK cells was dependent on perforin, as the addition of the perforin inhibitor concanamycin-A abrogated cytotoxic activity against K562 cells (FIG. 5B). N-NK cells displayed moderate perforin expression by flow cytometry (FIG. 5C) and morphologic assessment of N-NK cells by light microscopy demonstrated the presence of cytoplasmic granules, consistent with a large granular lymphocyte morphology (not shown). We also tested the cytotoxic function of NK cells from control co-cultures without Notch ligand, after enriching these NK cells to percentages greater than 50% by negative cell selection. The cytotoxic function of NK cells developed in the absence of Notch ligand was similar to that of N-NK cells: when compared side by side, the average percent specific lysis for K562 cells was 45.7% for NK cells grown in the presence of Delta4 vs. 50.1% for NK cells grown in the absence of Notch ligand (E:T ratio of 7:1), and 34.2% vs. 28.5%, respectively, for killing of RPMI-8226 cells (E:T ratio of 7:1).

We next compared the cytotoxic function of N-NK cells with peripheral blood (PB) NK cells, either unstimulated or activated overnight with IL-15 (10 ng/ml). Interestingly, the killing activity of N-NK cells against K562 and RPMI-8226 was similar to activated PB NK cells (FIG. 5D), while only activated PB NK had activity against Daudi cells. This was in contrast to unstimulated PB NK (cultured overnight without IL-15), which had the lowest capacity of the three types of NK cells for killing of K562, RPMI-8226, or Daudi. Thus, although N-NK cells lack cytotoxic function against Daudi cells, the killing activity of two other cell lines was more similar to that of stimulated PB NK cells than unstimulated.

Figure 6:
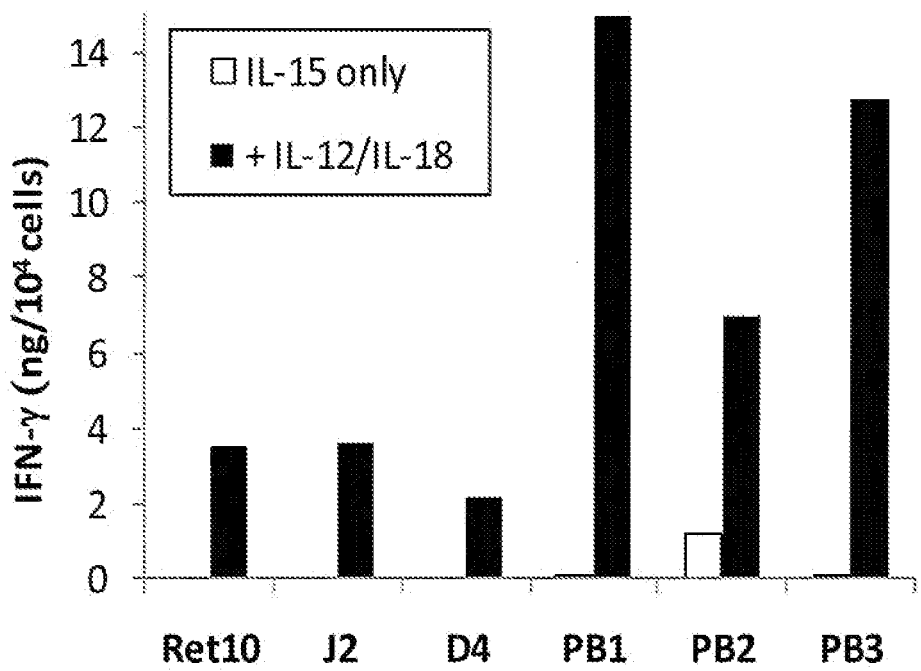
FIG. 6 illustrates that both N-NK cells and NK cells developed in the absence of Notch ligand can secrete IFN-γ only after overnight incubation with IL-12 and IL-18 (100 ng/ml each). Levels of IFN-γ secreted by PB NK cells from three different healthy donors are shown for comparison. PB NK cells were cultured for two days in the presence of IL-15, with or without additional IL-12 and IL-18 on day 2.

To evaluate the ability of N-NK cells to secrete cytokines, IFN-γ in co-culture supernatants was measured by standard ELISA. In the absence of IL-12 and IL-18, neither NK cells developed in the absence or presence of Notch signaling secreted IFN-γ, similar to most PB NK cells cultured in IL-15 alone (FIG. 6). However, overnight incubation with IL-12 and IL-18 resulted in secretion of IFN-γ by both N-NK cells and NK cells developed in the absence of Notch ligand (FIG. 6), albeit at lower levels than IL-15-activated PB NK cells further stimulated with IL-12 and IL-18.

Overall, these data indicate that although the surface phenotype of N-NK cells resembles that of an immature NK cell precursor (CD56bright, CD117+, CD16−, CD94−, KIR−, CD11b−), the N-NK cells have the functional characteristics of both CD56bright and CD56dim NK cells, i.e. cytokine secretion and cytotoxic ability, respectively, with the cytotoxic capacity of N-NK cells being similar but not identical to activated PB NK cells.

Example 2

Recombinant, Immobilized Delta4 Can Induce NK Cell Differentiation and Expansion from CD34+ HPCs The marked expansion of N-NK cells caused by Notch, in addition to the unique phenotype and functionality of these cells, suggest that N-NK cells have potential use as cell therapy agents against malignancy. In order to generate a culture system that would translate more readily to clinical use, we explored the ability of purified recombinant Notch ligand to induce differentiation and expansion of NK cells from CD34+ HPCs. Purified, immobilized Delta1 has been used both to expand primitive HPCs and to induce T cell differentiation in vitro. Moreover, the use of purified ligands allows for the 1) titration of Notch ligand concentrations, as different ligand densities may affect cellular outcome and 2) precise comparison of different Notch ligands to generate NK cells, since distinct Notch ligands have differential capacity to induce cell differentiation. While we noted that recombinant Notch ligand bound to the bottom of tissue culture wells is capable of inducing NK cell differentiation from CD34+ HPCs (data not shown), we decided to use Protein A beads from Dynal as the solid substrate for Notch ligand because of the increased surface area and a precedent for the use of anti-CD3/CD28 Dynal bead culture for T cell expansion for cell therapeutic use.

Figure 7:
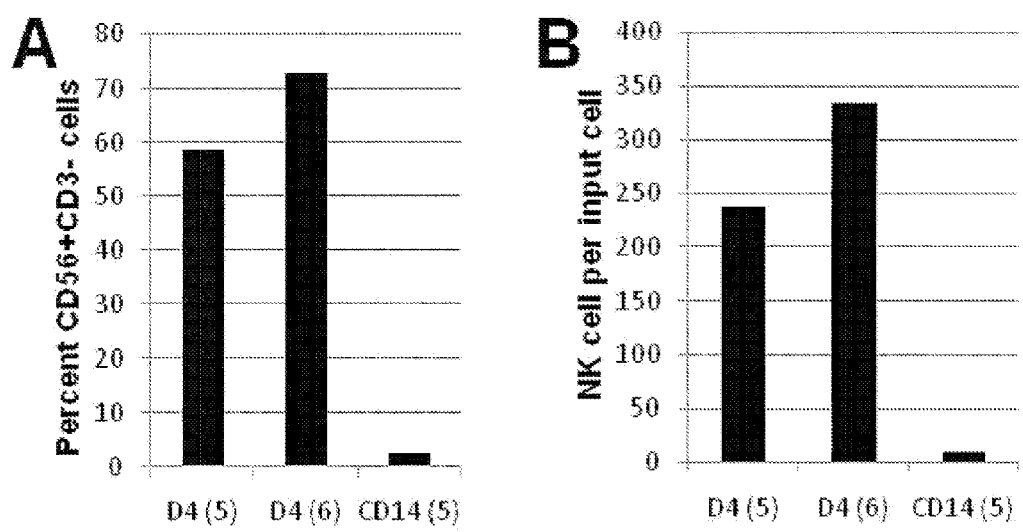
FIG. 7 illustrates that bead-bound Delta4 induces NK cell differentiation (A) and expansion (B) from human HPCs. $CD34^+$ HPCs were cultured with Delta4-beads in the presence of IL-7, FL, SCF, IL-15, and IL-3 [D4 (5)] or the 5 cytokines plus IL-6 [D4 (6)]. CD14-beads were used as a negative control [CD14 (5)] Percentage and absolute numbers of NK cells were determined at 3.5 weeks of culture. Data are representative of 2 individual experiments.

A recombinant DNA construct composed of the extracellular domain of Delta4 fused with the Fc region of human IgG1 was provided kindly by Dr. John Lowe (now at Genentech, San Franscisco). Transcription of the construct results in a chimeric protein designated as Delta4:Fc. We transfected the construct into HEK293T cells using standard transfection procedures. The presence of Delta4:Fc in the supernatant was verified by both Western Blot and ELISA using antibodies against human IgG1 Fc. The supernatant was then concentrated and incubated with Protein A Dynal beads per manufacturer instructions. The amount of chimera bound to the beads was determined using ELISA to measure the amount of protein present in pre- and post-bind supernatants. We then cultured CD34+ HPCs with the Delta4-beads at 0.33 μg/ml culture, in the presence of a combination of five (IL-7, FL, SCF, IL-15, IL-3) or six (the previous 5, plus IL-6) cytokines. Preliminary experiments have demonstrated that after 3-4 weeks of culture, the bead-bound Delta4 is capable of inducing NK cell differentiation and expansion, although the expansion is lower than that seen in the OP9 co-culture system (FIG. 7). The percentage of NK cells reached up to 91% after 4 weeks of culture.

Figure 8:
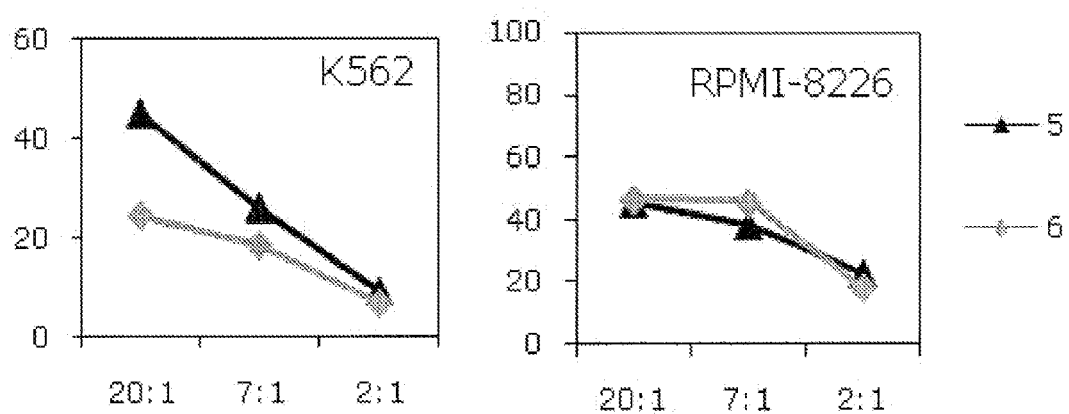
FIG. 8 illustrates a graphical representation of the cytotoxic ability of NK cells from day 24 of the Delta4-bead culture. "5" or "6" denotes cells grown in the presence of 5 or 6 cytokines, respectively. Percent specific lysis is the value of the y axis; Effector:Target ratio is the x axis. K562 is an acute myeloid leukemia line; RMPI-8226 is a myeloma line.
Figure 9C:
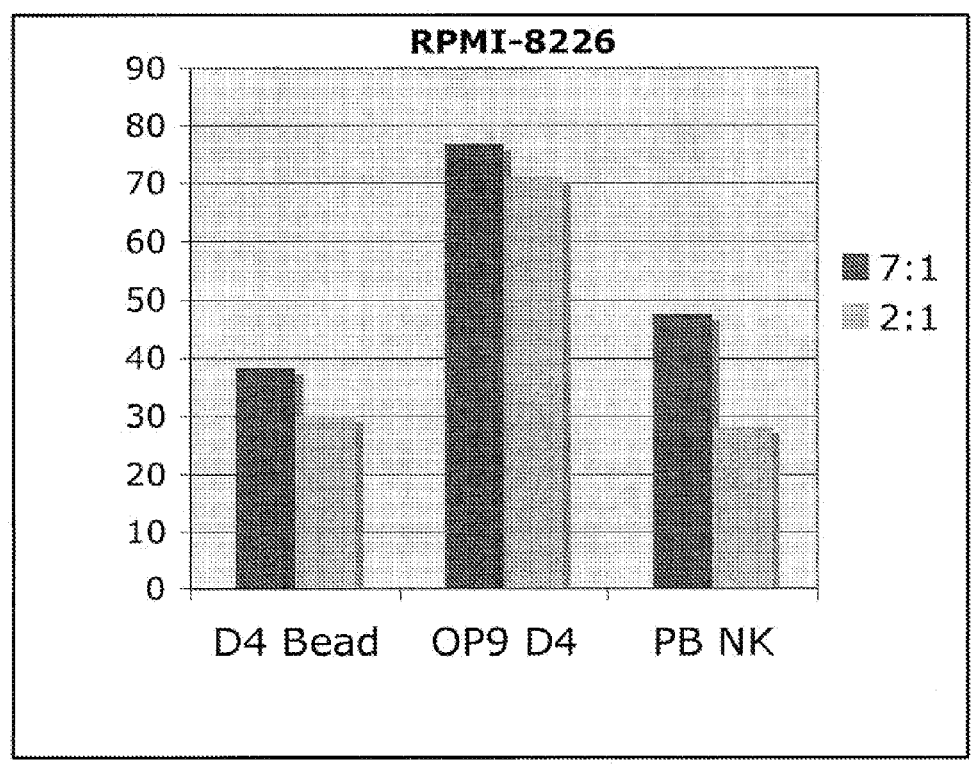
FIG. 9 illustrates a graphical representation comparing the cytotoxic ability of NK cells generated from the Delta4-bead culture (D4 Bead), NK cells generated from OP9 D4 cells (OP9 D4), and activated peripheral blood NK cells (PB NK) in killing hematopoietic tumor cell lines (K562, Jurkat, RPMI-8226). Light grey bars represent an Effector:Target ratio of 2:1, dark grey bars represent an Effector:Target ratio of 7:1.

FIG. 8 demonstrates cytoxic ability of NK cells from day 24 of the delta4-bead culture. "5" or "6" denotes cells grown in the presence of 5 or 6 cytokines, respectively. Percent specific lysis the value of the y axis; effetor:targe ratio is the x axis. K562 is an acute myeloid leukemia cell line and RMPI-8226 is a myeloma cell line.

Example 3

HEK 293T cells were transfected with a vector encoding a chimeric molecule consisting of the outer membrane component of murine Delta4 fused with human IgG1 Fc, termed Delta4:Fc. The presence of the Delta4:Fc chimera in the cell supernatant was verified by Western Blot and quantified by ELISA using anti-human Fc antibody. Concentrated supernatant was combined with Protein A microbeads for a target concentration of 40-60 ng Delta4:Fc per μl of beads. The amount of Delta4:Fc bound to the beads was confirmed by ELISA performed on the post-bind supernatant. Delta4-beads were incubated with CD34+ HPCs isolated from cord blood, in the presence of cytokines including IL-7 and IL-15 to promote NK cell development. A commercially available chimera, CD14:Fc, was also bound to beads and served as a negative control. After 14 days, cultures were monitored weekly by flow cytometry for the development of NK (CD56+CD3−) cells. Receptor phenotype of NK cells was determined by flow cytometry, and the ability of NK cells to lyse hematopoietic tumor cell lines was examined by a non-radioactive cytotoxicity assay (Promega CytoTox-Glo™).

Results

Incubation of CD34+ HPCs with 0.33 μg/well Delta4:Fc in the presence of IL-7, SCF, Flt-3L, IL-3, and IL-15 resulted in an average of 73.4% NK cells after 21 days in culture, with the percentage reaching up to 90% in some experiments after 28 days. The non-NK cells in culture consisted of CD33+ granulocytes; no T cells or B cells were seen. Expansion of NK cells reached an average of 248-fold after 28 days in culture. The addition of IL-6 to the above 5-cytokine mix increased the expansion of NK cells to 334-fold, although the percentage of NK cells was only marginally increased. NK cell development and expansion was specific to the presence of Delta4, as cultures containing CD14:Fc-beads routinely resulted in less than 5% NK cells and less than 10-fold NK cell expansion. The receptor phenotype of NK cells derived from the Delta4-bead system included expression of the natural cytotoxicity receptors (NKp30,44,46) and CD244 (2B4), absent/low expression of CD16 and NKG2D, and absence of the inhibitory receptors KIR and NKG2A. This phenotype is similar to that previously reported for NK cells cultured with Delta4-expressing OP-9 stromal cells.

NK cells from the bead system were capable of lysing various human hematopoietic tumor cell lines (K562, RPMI-8226, and OCI-AML3). The functionality of NK cells from the bead system ("D4 Bead") was then compared with Notch-induced NK cells from the OP9-D4 coculture system ("OP9 D4") and activated peripheral blood NK cells (PB NK; cultured overnight in the presence of IL-15).

Figure 10:
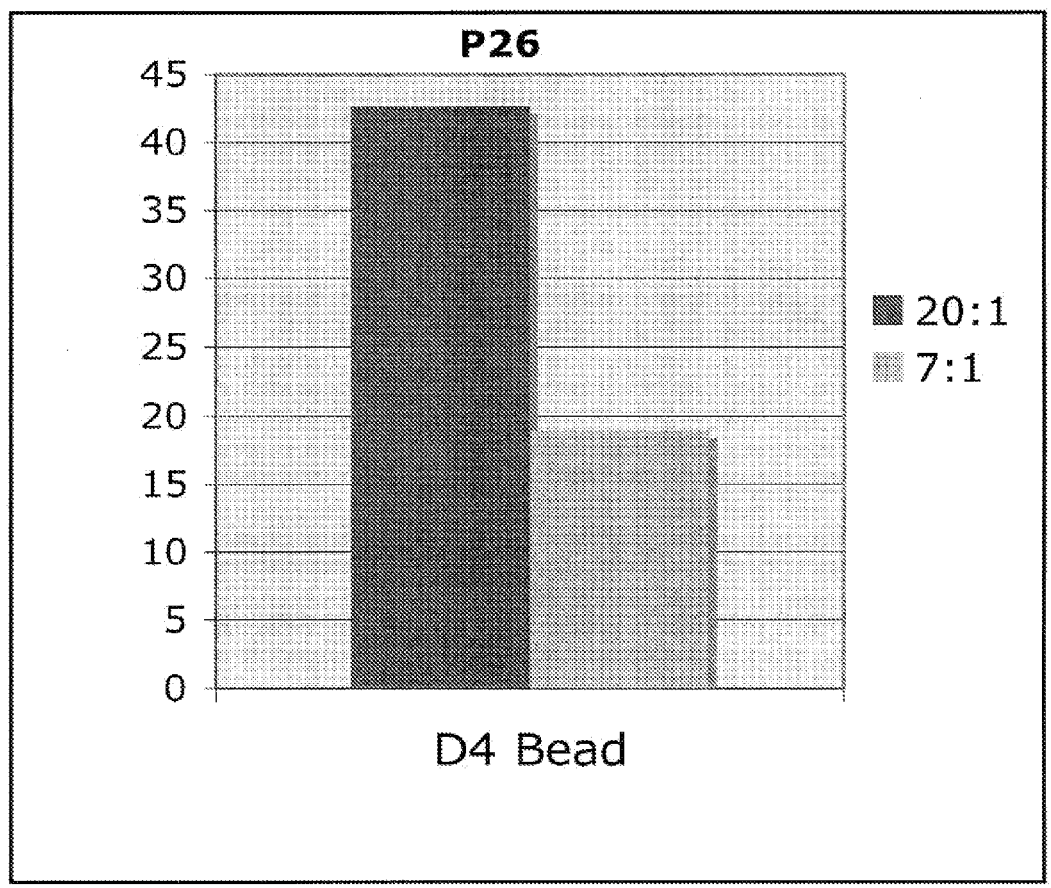
FIG. 10 illustrates a graphical representation of the cytotoxic ability of NK cells generated from the Delta4-bead culture (D4 Bead) in killing acute myeloid leukemia (AML) cells. Light grey bars represent an Effector:Target ratio of 7:1, dark grey bars represent an Effector:Target ratio of 20:1.

The data shown in FIGS. 9-12 is obtained from standard cytotoxicity assays using the non-radioactive Promega Cyto-Tox Glo kit, with incubation time of 6 or 8 hours. FIGS. 9A-C illustrates the killing of hematopoietic tumor cell lines. Comparison between all 3 types of NK cells-cytotoxic activity is similar. FIG. 10 illustrates the killing of primary AML cells by D4 Bead cells. Note change in E;T ratios shown (the more linear part of the cytotoxicity assay curve is included in the bar graphs). Each "P" is a different AML patient. FIGS. 11(A-B) illustrate the killing of primary AML cells, comparison between bead and PB NK (A) or all 3 types of NK cells (B). The Notch NK cells have similar or lower cytotoxic capacity than the activated PB NK cells, depending on the patient. FIGS. 12 (A-B) show further comparison of killing activity of all 3 types of NK cells using cell from two more patients.

Accordingly, recombinant Delta4 immobilized onto microbeads is capable of inducing expansion and differentiation of functional, inhibitory receptor-negative NK cells from CD34$^+$ HPCs, independent of the presence of stromal cells. The Delta4-bead culture may be a practical strategy for the generation and expansion of NK cells for cell therapy purposes.

From the above description of the invention, those skilled in the art will perceive improvements, changes and modifications. Such improvements, changes, and modifications are within the skill of the art and are intended to be covered by the appended claims. All patents, patent applications, and publications cited herein are incorporated by reference in their entirety.

Having described the invention, the following is claimed:

1. A method of preparing differentiated NK cells by ex vivo expansion comprising:
   isolating a plurality of CD 34+ hematopoietic cells;
   culturing the cells in a medium free of stromal cells, wherein the medium includes an effective amount of a notch ligand and IL-7, IL-15, SCF, Flt-3 and IL-3, the notch ligand being immobilized on a solid substrate that facilitates interaction of the CD34+ cells and the notch ligand, wherein the solid substrate is suspended in the medium; and
   maintaining the cells in culture for a duration of time sufficient to produce NK cells.

2. The method of claim 1, the notch ligand comprising delta4 notch ligand.

3. The method of claim 1, wherein the NK cells lack MHC class I inhibitory signals.

4. The method of claim 1, wherein the NK cells do not express an inhibitory receptor surface protein selected from KIR and NKG2A.

5. The method of claim 1, the solid substrate comprising a plurality of protein A beads.

6. The method according to claim 5, wherein the protein A beads are used at a concentration of at least 0.01 µg/ml to 100 µg/ml.

7. The method of claim 1 wherein the hematopoietic cells are derived from umbilical cord blood.

8. The method of claim 1, the medium further comprising IL-6.

9. The method of claim 1, the predetermined time period comprising between about 2 weeks and about 6 weeks.

10. The method of claim 1, wherein the NK cells have at least the following characteristics: CD56$^{bright}$, CD16$^-$, CD117$^+$, KIR$^-$, CD94$^{low}$, CD11b−.

* * * * *